(12) United States Patent
Krasnoslobodtsev et al.

(10) Patent No.: US 11,257,594 B1
(45) Date of Patent: Feb. 22, 2022

(54) SYSTEM AND METHOD FOR BIOMARKER-OUTCOME PREDICTION AND MEDICAL LITERATURE EXPLORATION

(71) Applicant: Ro5 Inc., Dallas, TX (US)

(72) Inventors: Artem Krasnoslobodtsev, Frisco, TX (US); Danius Jean Backis, Vilnius (LT); Pouya Babakhani, Berlin (DE); Žygimantas Jočys, Hove (GB); Roy Tal, Dallas, TX (US); Charles Dazler Knuff, Dallas, TX (US)

(73) Assignee: RO5 INC., Dallas, TX (US)

( * ) Notice: Subject to any disclaimer, the term of this patent is extended or adjusted under 35 U.S.C. 154(b) by 0 days.

(21) Appl. No.: 17/177,565

(22) Filed: Feb. 17, 2021

Related U.S. Application Data

(63) Continuation-in-part of application No. 17/175,832, filed on Feb. 15, 2021, which is a continuation-in-part
(Continued)

(51) Int. Cl.
*G06G 7/58* (2006.01)
*G16H 50/70* (2018.01)
(Continued)

(52) U.S. Cl.
CPC ......... *G16H 50/70* (2018.01); *G06F 16/2465* (2019.01); *G06F 40/279* (2020.01);
(Continued)

(58) Field of Classification Search
CPC ........ G16H 50/70; G16H 10/20; G16H 70/40; G06F 16/2465; G06F 40/279; G06F 2216/03; G16B 40/00
(Continued)

(56) References Cited

U.S. PATENT DOCUMENTS

| | | | |
|---|---|---|---|
| 2014/0142861 A1* | 5/2014 | Hagstrom | C12Q 1/6883 702/19 |
| 2015/0278901 A1* | 10/2015 | Windemuth | G06Q 30/0621 705/26.5 |

(Continued)

*Primary Examiner* — Charlotte M Baker
(74) *Attorney, Agent, or Firm* — Galvin Patent Law LLC; Brian R. Galvin

(57) ABSTRACT

A system and method for biomarker-outcome prediction and medical literature exploration which utilizes a data platform to analyze, optimize, and explore the knowledge contained in or derived from clinical trials. The system utilizes a knowledge graph and data analysis engine capabilities of the data platform. The knowledge graph may be used to link biomarkers with molecules, proteins, and genetic data to provide insight into the relationship between biomarkers, outcomes, and adverse events. The system uses natural language processing techniques on a large corpus of medical literature to perform advanced text mining to identify biomarkers associated with adverse events and to curate a comprehensive profile of biomarker-outcome associations. These associations may then be ranked to identify the most-common biomarker-outcome association pairs. Having a comprehensive profile of ranked biomarker-outcome data allows the system to predict biomarkers associated with a given disease and serious adverse events linked to biomarker data.

2 Claims, 22 Drawing Sheets

Related U.S. Application Data of application No. 17/174,677, filed on Feb. 12, 2021, which is a continuation-in-part of application No. 17/171,494, filed on Feb. 9, 2021, which is a continuation-in-part of application No. 17/166,435, filed on Feb. 3, 2021, now Pat. No. 11,080,607.

(60) Provisional application No. 63/136,556, filed on Jan. 12, 2021, provisional application No. 63/135,892, filed on Jan. 11, 2021, provisional application No. 63/126,388, filed on Dec. 16, 2020, provisional application No. 63/126,372, filed on Dec. 16, 2020, provisional application No. 63/126,349, filed on Dec. 16, 2020.

(51) Int. Cl.
*G16H 70/40* (2018.01)
*G06F 40/279* (2020.01)
*G06F 16/2458* (2019.01)
*G16B 40/00* (2019.01)
*G16H 10/20* (2018.01)

(52) U.S. Cl.
CPC ............ *G16B 40/00* (2019.02); *G16H 10/20* (2018.01); *G16H 70/40* (2018.01); *G06F 2216/03* (2013.01)

(58) Field of Classification Search
USPC .......................................................... 703/11
See application file for complete search history.

(56) References Cited

U.S. PATENT DOCUMENTS

| | | |
|---|---|---|
| 2016/0342753 A1 | 11/2016 | Feazell |
| 2018/0082197 A1* | 3/2018 | Aravamudan ......... G06N 5/022 |
| 2019/0156946 A1 | 5/2019 | Ulain et al. |
| 2020/0411199 A1 | 12/2020 | Shrager et al. |

* cited by examiner

SYSTEM AND METHOD FOR BIOMARKER-OUTCOME PREDICTION AND MEDICAL LITERATURE EXPLORATION

CROSS-REFERENCE TO RELATED APPLICATIONS

| Application No. | Date Filed | Title |
|---|---|---|
| Current application | Herewith | DATA PLATFORM FOR AUTOMATED PHARMACEUTICAL RESEARCH USING KNOWLEDGE GRAPH |
| | | Claims benefit of, and priority to: |
| 63/136,556 | Jan. 12, 2021 | SYSTEM AND METHOD FOR BIOMARKER-OUTCOME PREDICTION AND MEDICAL LITERATURE EXPLORATION |
| | | and is also a continuation-in-part of: |
| 17/175,832 | Feb. 15, 2021 | SYSTEM AND METHOD FOR THE PREDICTION OF PHARMACOLOGICAL PROPERTIES USING MACHINE LEARNING |
| | | Claims benefit of, and priority to: |
| 63/135,892 | Jan. 11, 2021 | SYSTEM AND METHOD FOR THE PREDICTION OF PHARMACOLOGICAL PROPERTIES USING MACHINE LEARNING |
| | | and is also a continuation-in-part of: |
| 17/174,677 | Feb. 12, 2021 | SYSTEM AND METHOD FOR DE NOVO DRUG DISCOVERY |
| | | which claims benefit of, and priority to: |
| 63/126,388 | Dec. 16, 2020 | SYSTEM AND METHOD FOR DE NOVO DESIGN OF RECEPTOR-LIGAND PAIRS |
| | | and is also a continuation-in-part of: |
| 17/171,494 | Feb. 9, 2021 | SYSTEM AND METHOD FOR PREDICTION OF PROTEIN-LIGAND INTERACTIONS AND THEIR BIOACTIVITY |
| | | which claims benefit of, and priority to: |
| 63/126,372 | Dec. 16, 2020 | SYSTEM AND METHOD FOR PREDICTION OF PROTEIN-LIGAND INTERACTIONS AND THEIR BIOACTIVITY |
| | | and is also a continuation-in-part of: |
| 17/166,435 | Feb. 3, 2021 | DATA PLATFORM FOR AUTOMATED PHARMACEUTICAL RESEARCH USING KNOWLEDGE GRAPH |
| | | which claims benefit of, and priority to: |
| 63/126,349 | Dec. 16, 2020 | DATA PLATFORM FOR AUTOMATED PHARMACEUTICAL RESEARCH USING KNOWLEDGE GRAPH | the entire specification of each of which is incorporated herein by reference.

BACKGROUND

Field of the Art

The disclosure relates to the field of medical research, and more particularly to the field of biomarker-outcome prediction using association score and analysis.

Discussion of the State of the Art

A large amount of biomarker-outcome associations are observed empirically and are publicly available through a quick internet search. However, there is still a vast amount of biomarker-outcome associations buried in the biomedical literature. Given the large amount of literature data, it is untenable to manually curate biomarker-outcome associations. Furthermore, it is almost impossible to know the most recent information about how each biomarker is related to each outcome. Compounding these issues is the lack of a user friendly navigable interface for exploring the large amount historical clinical trial data contained within the biomedical literature.

What is needed is a system and method for biomarker-outcome prediction and medical literature exploration which utilizes an automated text mining tool to automatically curate a comprehensive list of biomarker-outcome pairs, which calculates an association score for each biomarker-outcome pair, which can provide context between the relationship between biomarker and outcome, and which provides a user interface for exploring the literature.

SUMMARY

Accordingly, the inventor has conceived and reduced to practice, a system and method for biomarker-outcome prediction and medical literature exploration which utilizes a data platform to analyze, optimize, and explore the knowledge contained in or derived from clinical trials. The system utilizes a knowledge graph and data analysis engine capabilities of the data platform. The knowledge graph may be used to link biomarkers with molecules, proteins, and genetic data to provide insight into the relationship between biomarkers, outcomes, and adverse events. The system uses natural language processing techniques on a large corpus of medical literature to perform advanced text mining to identify biomarkers associated with adverse events and to curate a comprehensive profile of biomarker-outcome associations. These associations may then be ranked to identify the most-common biomarker-outcome association pairs. Having a comprehensive profile of ranked biomarker-outcome data allows the system to predict biomarkers associated with a given disease and serious adverse events linked to biomarker data.

According to a preferred embodiment, a system for calculating an association score between a biomarker and some outcome, is disclosed, comprising: a computing device comprising a memory and a processor; a database comprising clinical trial publications; an automated text mining tool comprising at first plurality of programming instructions stored in the memory and operating on the processor of, wherein the first plurality of programming instructions, when operating on the processor, causes the computing device to: receive a clinical trial publication; scrape the clinical trial publications for biomarker and outcome word pairs; compute the total number of times the outcome word appears after the biomarker word in a window of words for all clinical trial publications; an association calculator comprising at first plurality of programming instructions stored in the memory and operating on the processor of, wherein the first plurality of programming instructions, when operating on the processor, causes the computing device to: compute the probability of occurrence for each biomarker by dividing the computed total number of times each biomarker appears in all papers by the total number of publications in the database; compute the probability of occurrence for each outcome by dividing the computed total number of times each outcome appears in all papers by the total number of publications in the database; compute the probability of each biomarker occurring with each outcome word by dividing the computed total number of times the outcome word appears after the biomarker word by the total number of publications in the database; and compute the association score for each biomarker and outcome word pair via normalized pointwise mutual information for each biomarker and outcome word pair using the probability of occurrence for each biomarker, the probability of occurrence for each outcome, and the probability each biomarker occurring with each outcome.

According to a preferred embodiment, a method for calculating an association score between a biomarker and some outcome, is disclosed, comprising the steps of: receiving a clinical trial publication; scraping the clinical trial publications for biomarker and outcome word pairs; computing the total number of times the outcome word appears after the biomarker word in a window of words for all clinical trial publications; computing the probability of occurrence for each biomarker by dividing the computed total number of times each biomarker appears in all papers by the total number of publications in the database; computing the probability of occurrence for each outcome by dividing the computed total number of times each outcome appears in all papers by the total number of publications in the database; computing the probability of each biomarker occurring with each outcome word by dividing the computed total number of times the outcome word appears after the biomarker word by the total number of publications in the database; and computing the association score for each biomarker and outcome word pair via normalized pointwise mutual information for each biomarker and outcome word pair using the probability of occurrence for each biomarker, the probability of occurrence for each outcome, and the probability each biomarker occurring with each outcome.

BRIEF DESCRIPTION OF THE DRAWING FIGURES

The accompanying drawings illustrate several aspects and, together with the description, serve to explain the principles of the invention according to the aspects. It will be appreciated by one skilled in the art that the particular arrangements illustrated in the drawings are merely exemplary, and are not to be considered as limiting of the scope of the invention or the claims herein in any way.

DETAILED DESCRIPTION

Figure 1:
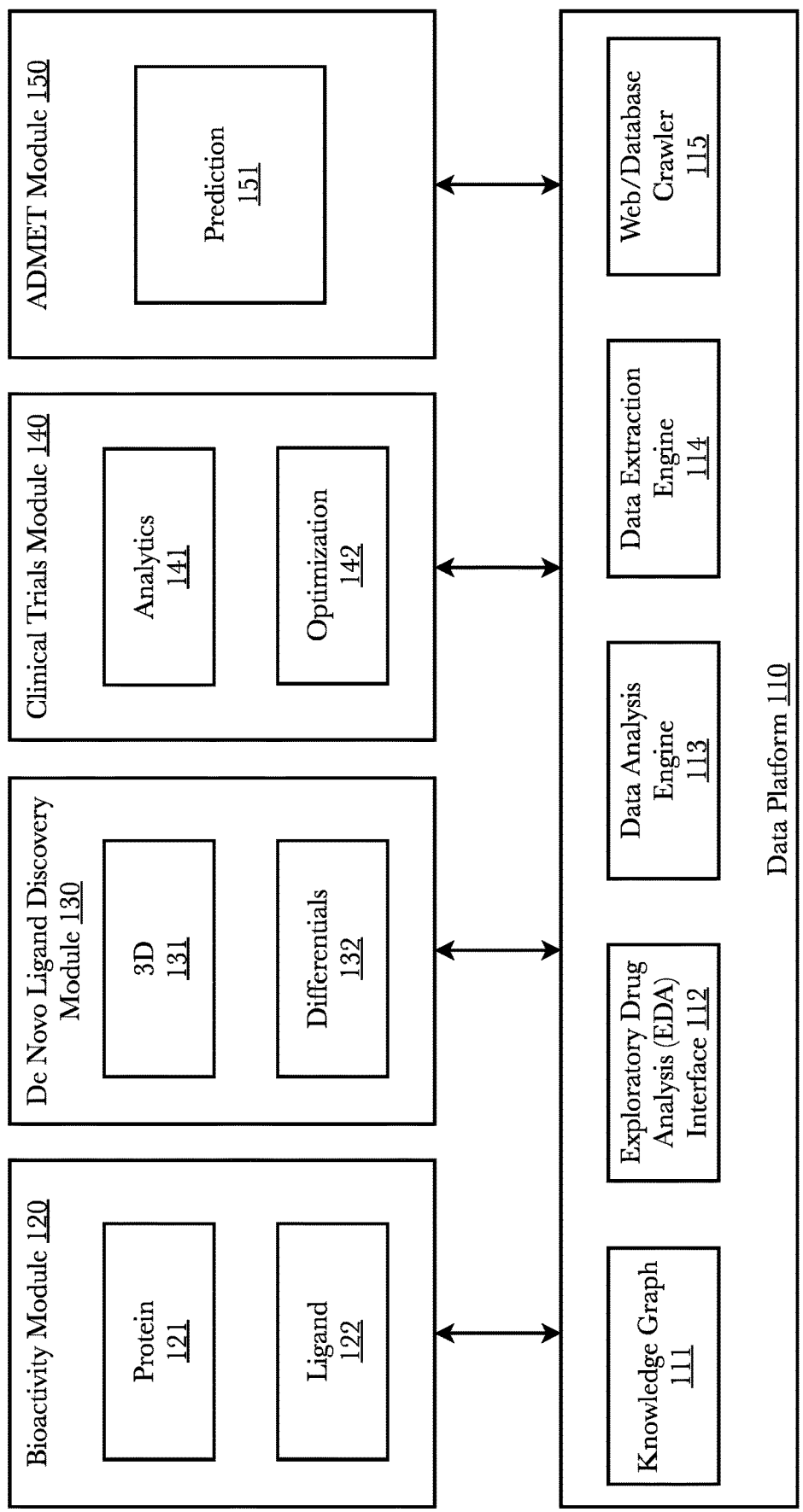
FIG. 1 is a block diagram illustrating an exemplary overall system architecture for a pharmaceutical research system.

The inventor has conceived, and reduced to practice, a system and method for biomarker-outcome prediction and medical literature exploration which utilizes a data platform to analyze, optimize, and explore the knowledge contained in or derived from clinical trials. The system utilizes a knowledge graph and data analysis engine capabilities of the data platform. The knowledge graph may be used to link biomarkers with molecules, proteins, and genetic data to provide insight into the relationship between biomarkers, outcomes, and adverse events. The system uses natural language processing techniques on a large corpus of medical literature to perform advanced text mining to identify biomarkers associated with adverse events and to curate a comprehensive profile of biomarker-outcome associations. These associations may then be ranked to identify the most-common biomarker-outcome association pairs. Having a comprehensive profile of ranked biomarker-outcome data allows the system to predict biomarkers associated with a given disease and serious adverse events linked to biomarker data.

A large plurality of biomarkers-outcomes associations are observed empirically and are publicly available through a quick internet search. A few examples of such associations are high cholesterol-high blood pressure, high cholesterol-heart failure, or elevated glucose level-chronic constipation. However, there is still a vast amount of biomarker-outcome associations buried in the biomedical literature. The clinical trial prediction and exploration system may leverage the massive corpus of pharmaceutical information, particularly data extracted from biomedical literature, and implement an automated text mining tool to curate biomarker-outcome associations and parse clinical trials into a data format that allows for easy exploration of historical clinical trial data.

The data platform may utilize a natural language processing (NLP) based automated text mining tool which scrapes medical literature (e.g., clinical trial, assay, and research publications) to populate the data fields of a standard clinical trial data model. The standard clinical trial data model may include data fields for clinical trial information including, but not limited to, publication title, geolocation data identifying the research center or institute which conducted the clinical trial, the trial phase in which the clinical trial ended, date of publication, a link to the original publication, biomarkers studied or identified during research, outcomes predicted and observed, population sample size, population demographics, and medical intervention of interest such as pharmaceutical drug or treatment process. Most clinical trials are regulated and standardized via a set of rules and procedures defined by some regulatory or governmental organization, for instance, the Federal Drug Administration. As a result, a standard clinical trial data model may be developed and utilized by the system to organize the information contained within clinical trial publications and to facilitate easier exploration of historical clinical trial data via a knowledge graph. A clinical trial may be scraped and a standard data model of the clinical trial is generated which is then persisted to a knowledge graph which may be traversed to explore all available clinical trial data. For example, the system may be queried to provide all clinical trials conducted and published by a specified research center. Similarly, the system may be queried to identify all outcomes associated with one or more specified biomarkers. The standard clinical trial data model may also allow for exploration of historical clinical trial data using one or more of the data fields, for example the system may be queried to return all clinical trials published in a given year, or range of years.

The clinical trial prediction and exploration system may allow a client (pharmaceutical company, contract research organization, etc.), who is interested in running a clinical trial, to input a list of biomarkers that will be measured during screening or continuously throughout a clinical trial for each patient. The system, utilizing the automated text mining tool, may return for each biomarker a list of papers that contain associations between that biomarker and side effects, diseases, adverse events, etc. In addition to the list of papers, the system may calculate and return an association score between a biomarker and some outcome. The association score may be derived from calculating the co-occurrence of a biomarker and some outcome across all available medical literature using an automated text mining tool. Ranking biomarker-outcome associations allows the system to link biomarkers to serious adverse events which provides a new and useful tool for developing and analyzing genetic profiles of patients. Furthermore, ranking biomarker-outcome associations allows the system to suggest adverse events that may be predicted from the biomarker data.

By combining a standard data model with the linked and ranked biomarker-adverse event associations the system may facilitate demographic based queries to attain new insights derived from historical clinical trial data. For example, the system may receive as input a list of biomarkers such as chronic heart failure, Caucasian (a subset of population), and cholesterol and return a list of papers that provide relevant information for that subset of the population in the context of the other biomarkers. In an embodiment, to help with clinical trial design the system may identify at-risk populations based on biomarkers and trial drug characteristics. For instance, a biomarker may be associated with some biological process and the biological process may be regulated by certain proteins and furthermore, the protein function may be impacted by some molecule which may be present in a drug. Using the data platform knowledge graph the system may be able quickly identify the connection, via biological pathways, between a biomarker and a trial drug. At-risk populations may be selected based upon identified biological pathways that may be compromised due to underlying conditions, genetics, physical disposition, etc. For example, a population with low blood pressure biomarkers could be considered an at-risk population for a drug that purports to lower blood pressure to cause some effect.

One of the key aspects of planning a useful and meaningful clinical trial is sample size estimation. Underestimation of sample size may result in a drug turning out to be statistically non-significant even though clinical significance exists. Over estimation of sample size may lead to other issues that should be considered: a smaller sample size may have been used to prove statistical significance which can raise ethical issues as more test subjects were exposed to the test drug, which could have deserved trialing the new drug being researched, and a large sample size may mean even a small difference between the trial drug and the test drug will turn out statistically significant even if that difference is not clinically meaningful. Therefore, sample size is an important factor for approval or rejection of clinical trial results regardless of how clinically effective or ineffective the test drug may be. Typical sample size estimation depends on a few basic requirements including, but not limited to, Types I and II error and Power, study design (e.g., parallel group, crossover group, etc.), study endpoint and its description (e.g., discrete, time-to-event, continuous, etc.), expected response test versus control, clinical meaningful margin which defines the difference between test and reference which can be considered clinically meaningful, level of significance (typically value is 5% or less), and participant drop-out rate. The clinical trial prediction and exploration system may feature a sample size calculator with the prior information sampled from the historical clinical trial data based on locations of the previous trials. In one embodiment, a system user may input singly or in some combination a biomarker, drug, disease, and information about a potential clinical trial such as the study design, a trial drug, and an endpoint and the system will retrieve historical clinical trial data related to and associated with the input and then analyze the data to estimate a sample size appropriate for producing statistically meaningful results.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

Definitions

"Bioactivity" as used herein means the physiological effects of a molecule on an organism, including but not limited to effects on substructures, organs, cells, proteins, or metabolic pathways of the organism.

"Edges" as used herein means connections between nodes or vertices in a data structure. In graphs, an arbitrary number of edges may be assigned to any node or vertex, each edge representing a relationship to itself or any other node or vertex. Edges may also comprise value, conditions, or other information, such as edge weights or probabilities.

"FASTA" as used herein means any version of the FASTA family (e.g., FASTA, FASTP, FASTA, etc.) of chemical notations for describing nucleotide sequences or amino acid (protein) sequences using text (e.g., ASCII) strings.

"Ligand" as used herein means a substance that forms a complex with a biomolecule to serve a biological purpose. In protein-ligand binding, the ligand is usually a molecule which produces a signal by binding to a site on a target protein. Ligand binding to a receptor protein alters the conformation by affecting the three-dimensional shape orientation. The conformation of a receptor protein composes the functional state. Ligands comprise substrates, inhibitors, activators, signaling lipids, and neurotransmitters.

"Nodes" and "Vertices" are used herein interchangeably to mean a unit of a data structure comprising a value, condition, or other information. Nodes and vertices may be arranged in lists, trees, graphs, and other forms of data structures. In graphs, nodes and vertices may be connected to an arbitrary number of edges, which represent relationships between the nodes or vertices. As the context requires, the term "node" may also refer to a node of a neural network (also referred to as a neuron) which is analogous to a graph node in that it is a point of information connected to other points of information through edges.

"Proteins" as used herein means large biomolecules, or macromolecules, consisting of one or more long chains of amino acid residues. Proteins perform a vast array of functions within organisms, including catalyzing metabolic reactions, DNA replication, responding to stimuli, providing structure to cells and organisms, and transporting molecules from one location to another. Proteins differ from one another primarily in their sequence of amino acids, which is dictated by the nucleotide sequence of their genes, and which usually results in protein folding into a specific 3D structure that determines its activity.

"SMILES" as used herein means any version of the "simplified molecular-input line-entry system," which is a form of chemical notation for describing the structure of molecules using short text (e.g., ASCII) strings.

"Biomarker" as used herein refers to anything that can be used as an indicator of a particular disease state or some other physiological state of a person. Biomarkers can be characteristic biological properties or molecules that can be detected and measured in parts of the body like the blood or tissue. For example, biomarkers may include, but are not limited to, high-cholesterol, blood pressure, specific cells, molecules, genes, gene products, enzymes, hormones, complex organ function, and general characteristic changes in biological structures.

"Outcome" as used herein is a measure within a clinical trial which is used to assess the effect, both positive and negative, of an intervention or treatment. In clinical trials such measures of direct importance of for an individual may include, but are not limited to, survival, quality of life, morbidity, suffering, functional impairment, and changes in symptoms.

"Normalized pointwise mutual information" (NPMI) as used herein is the measure of how much the actual probability of a particular co-occurrence of events (word-pairs) differs from its expected probability on the basis of the probabilities of the individual events and the assumption of independence. The calculated NPMI value is bounded between the values of negative one and one (−1, 1), inclusive. A value of negative one indicates the word-pair occur separately, but never occur together. A value of zero indicates independence of the word-pair in which co-occurrences happen at random. A value of one indicates complete co-occurrence, or that the word-pair only exist together.

Conceptual Architecture

FIG. 1 is a block diagram illustrating an exemplary overall system architecture for a pharmaceutical research system. The exemplary architecture comprises a data platform 110 which provides the core functionality of the system, plus one or more modules that utilize the data platform 110 to provide functionality in specific areas of research, in this case a bioactivity module 120, a de novo ligand discovery module 130, a clinical trials module 140, and an absorption, distribution, metabolism, excretion, and toxicity (ADMET) module 150.

The data platform 110 in this embodiment comprises a knowledge graph 111, an exploratory drug analysis (EDA) interface 112, a data analysis engine 113, a data extraction engine 114, and web crawler/database crawler 115. The crawler 115 searches for and retrieves medical information such as published medical literature, clinical trials, dissertations, conference papers, and databases of known pharmaceuticals and their effects. The crawler 115 feeds the medical information to a data extraction engine 114, which uses natural language processing techniques to extract and classify information contained in the medical literature such as indications of which molecules interact with which proteins and what physiological effects have been observed. Using the data extracted by the data extraction engine 114, a knowledge graph 111 is constructed comprising vertices (also called nodes) representing pieces of knowledge gleaned from the data and edges representing relationships between those pieces of knowledge. As a very brief example, it may be that one journal article suggests that a particular molecule is useful in treating a given disease, and another journal article suggests that a different molecule is useful for treating the same disease. The two molecules and the disease may be represented as vertices in the graph, and the relationships among them may be represented as edges between the vertices. The EDA interface 112 is a user interface through which pharmaceutical research may be performed by making queries and receiving responses. The queries are sent to a data analysis engine 113 which uses the knowledge graph 111 to determine a response, which is then provided to the user through the EDA interface 112. In some embodiments, the data analysis engine 113 comprises one or more graph-based neural networks (graph neural networks, or GNNs) to process the information contained in the knowledge graph 111 to determine a response to the user's query. As an example, the user may submit a query for identification of molecules likely to have similar bioactivity to a molecule with known bioactivity. The data analysis engine 113 may process the knowledge graph 111 through a GNN to identify such molecules based on the information and relationships in the knowledge graph 111.

The bioactivity module 120 utilizes the data platform 110 to analyze and predict the bioactivity of molecules based on protein 121 and ligand 122 similarities and known or suspected protein 121 and ligand 122 compatibilities. The module utilizes the knowledge graph 111 and data analysis engine 113 capabilities of the data platform 110, and in one embodiment is configured to predict the bioactivity of a molecule based on and their known or suspected compatibilities with certain combinations of proteins 121 and ligands 122. Thus, using the bioactivity module 120, users can research molecules by entering queries through the EDA interface 112, and obtaining using predictions of bioactivity based on known or suspected bioactivity of similar molecules and their compatibilities with certain protein 121 and ligand 122 combinations.

The de novo ligand discovery module 130 utilizes the data platform 110 to identify ligands and their properties through data enrichment and interpolation/perturbation. The module utilizes the knowledge graph 111 and data analysis engine 113 capabilities of the data platform 110, and in one embodiment is configured to identify ligands with certain properties based on three dimensional (3D) models 131 of known ligands and differentials of atom positions 132 in the latent space of the models after encoding by a 3D convolutional neural network (3D CNN), which is part of the data analysis engine 113. In one embodiment, the 3D model comprises a voxel image (volumetric, three dimensional pixel image) of the ligand. In cases where enrichment data is available, ligands may be identified by enriching the SMILES string for a ligand with information about possible atom configurations of the ligand and converting the enriched information into a plurality of 3D models of the atom. In cases where insufficient enrichment information is available, one possible configuration of the atoms of the ligand may be selected, and other configurations may be generated by interpolation or perturbation of the original configuration in the latent space after processing the 3D model through the CNN. In either case, the 3D models of the ligands are processed through a CNN, and a gradient descent is applied to changes in atom configuration in the latent space to identify new ligands with properties similar to the modeled ligands. Thus, using the de novo ligand discovery module 130, users can identify new ligands with properties similar to those of modeled ligands by entering queries through the EDA interface 112.

The clinical trials module 140 utilizes the data platform 110 to analyze 141 and optimize 142 the knowledge contained in or derived from clinical trials. The module utilizes the knowledge graph 111 and data analysis engine 113 capabilities of the data platform 110, and in one embodiment is configured to return clinical trials similar to a specified clinical trial in one or more aspects (e.g., proteins and ligands studied, methodology, results, etc.) based on semantic clustering within the knowledge graph 111. Thus, using the clinical trials module 140, users can research a large database of clinical trials based on aspects of interest by entering queries through the EDA interface 112.

The ADMET module 150 utilizes the data platform 110 to predict 151 absorption, distribution, metabolism, excretion, and toxicity characteristics of ligands based on ADMET databases. The module utilizes the knowledge graph 111 and data analysis engine 113 capabilities of the data platform 110, and in one embodiment is configured to return ligands with characteristics similar to, or dissimilar to, a specified ligand in one or more respects (e.g., a ligand with similar absorption and metabolism characteristics, but dissimilar toxicity characteristics) based on semantic clustering within the knowledge graph 111. Thus, using the ADMET module 150, users can research a large ADMET database based on aspects of interest by entering queries through the EDA interface 112.

Figure 2:
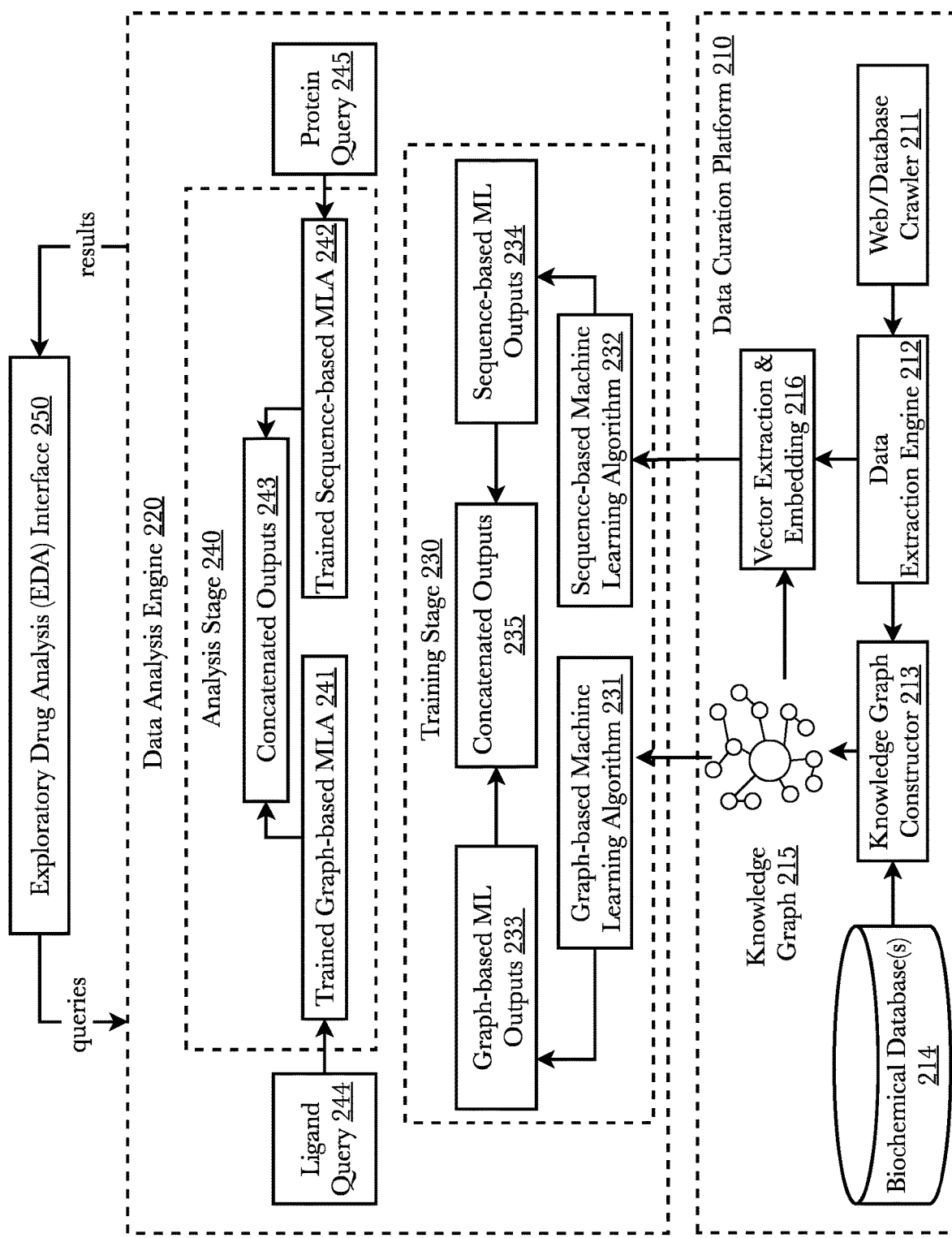
FIG. 2 is a block diagram illustrating an exemplary system architecture for an embodiment of a pharmaceutical research system utilizing combined graph-based and sequence-based prediction of molecule bioactivity.

FIG. 2 is a block diagram illustrating an exemplary system architecture for an embodiment of a pharmaceutical research system utilizing combined graph-based and sequence-based prediction of molecule bioactivity. In this embodiment, the system comprises a data curation platform 210, a data analysis engine 220 comprising a training stage 230 and an analysis stage 240, and an exploratory drug analysis interface 250.

In the data curation platform 210, a web crawler/database crawler 211 is configured to search for and download medical information materials including, but not limited to, archives of published medical literature such as MEDLINE and PubMed, archives of clinical trial databases such as the U.S. National Library of Medicine's ClinicalTrials.gov database and the World Health Organization International Clinical Trials Registry Platform (ICTRP), archives of published dissertations and theses such as the Networked Digital Library of These and Dissertations (NDLTD), archives of grey literature such as the Grey Literature Report, and news reports, conference papers, and individual journals. As the medical information is downloaded, it is fed to a data extraction engine 212 which may perform a series of operations to extract data from the medical information materials. For example, the data extraction engine 212 may first determine a format of each of the materials received (e.g., text, PDFs, images), and perform conversions of materials not in a machine-readable or extractable format (e.g., performing optical character recognition (OCR) on PDFs and images to extract any text contained therein). Once the text has been extracted from the materials, natural language processing (NLP) techniques may be used to extract useful information from the materials for use in analysis by machine learning algorithms. For example, semantic analysis may be performed on the text to determine a context of each piece of medical information material such as the field of research, the particular pharmaceuticals studied, results of the study, etc. Of particular importance is recognition of standardized biochemistry naming conventions including, but not limited to, stock nomenclature, International Union of Pure and Applied Chemistry (IUPAC) conventions, and simplified molecular-input line-entry system (SMILES) and FASTA text-based molecule representations. The data extraction engine 212 feeds the extracted data to a knowledge graph constructor 213, which constructs a knowledge graph 215 based on the information in the data, representing informational entities (e.g., proteins, molecules, diseases, study results, people) as vertices of a graph and relationships between the entities as edges of the graph. Biochemical databases 214 or similar sources of information may be used to supplement the graph with known properties of proteins, molecules, physiological effects, etc. Separately from the knowledge graph 215, vector representations of proteins, molecules, interactions, and other information may be represented as vectors 216, which may either be extracted from the knowledge graph 215 or may be created directly from data received from the data extraction engine 212.

The data analysis engine 220 utilizes the information gathered, organized, and stored in the data curation platform 210 to train machine learning algorithms at a training stage 230 and conduct analyses in response to queries and return results based on the analyses at an analysis stage 240. In this embodiment, the data analysis engine 220 comprises a dual analysis system which combines the outputs of a trained graph-based machine learning algorithm 241 with the outputs of a trained sequence-based machine learning algorithm 242. The trained graph-based machine learning algorithm 241 may be any type of algorithm configured to analyze graph-based data, such as graph traversal algorithms, clustering algorithms, or graph neural networks.

At the training stage 230, information from the knowledge graph 215 is extracted to provide training data in the form of graph-based representations of molecules and the known or suspected bioactivity of those molecules with certain proteins. The graph-based representations of the molecules and their associated bioactivities are used as training input data to a graph-based machine learning algorithm 231, resulting in a graph-based machine learning output 233 comprising vector representations of the characteristics of molecules and their bioactivities with certain proteins. Simultaneously, a sequence-based machine learning algorithm is likewise trained, but using information extracted 216 from the knowledge graph 215 in the form of vector representations of protein segments and the known or suspected bioactivity of those protein segments with certain molecules. The vector representations of the protein segments and their associated bioactivities are used as training input data to a sequence-based machine learning algorithm 232, resulting in a vector-based machine learning output 234 comprising vector representations of the characteristics of protein segments and their bioactivities with certain molecules. In this embodiment, the graph-based machine learning outputs 233 and the sequence-based machine learning outputs 234 are concatenated to produce a concatenated output 235, which serves to strengthen the learning information from each of the separate machine learning algorithms. In some embodiments, the concatenated output may be used to re-train both machine learning algorithms 233, 234 to further refine the predictive abilities of the algorithms.

At the analysis stage, a query in the form of a target ligand 244 and a target protein 245 are entered using an exploratory drug analysis (EDA) interface 250. The target ligand 244 is processed through the trained graph-based machine learning algorithm 241 which, based on its training, produces an output comprising a vector representation of the likelihood of interaction of the target ligand 244 with certain proteins and the likelihood of the bioactivity resulting from the interactions. Similarly, the target protein 245 is processed through the trained sequence-based machine learning algorithm 242 which, based on its training, produces an output comprising a vector representation of the likelihood of interaction of the target protein 245 with certain ligands and the likelihood of the bioactivity resulting from the interactions. The results may be concatenated 243 to strengthen the likelihood information from each of the separate trained machine learning algorithms 241, 242.

Figure 3:
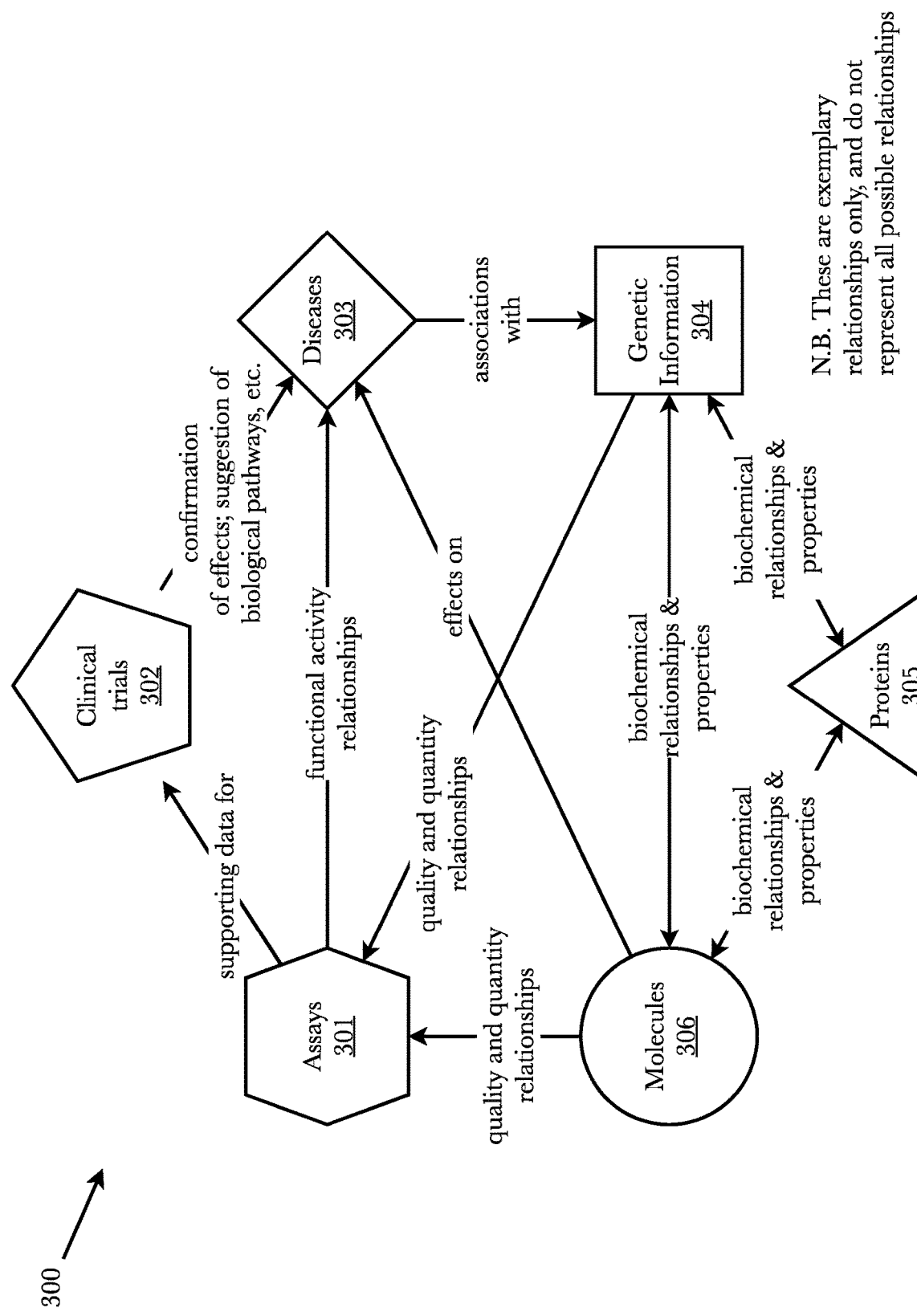
FIG. 3 is a relational diagram illustrating several types of information that may be included in a knowledge graph for a pharmaceutical research system and exemplary relations between those types of information.

FIG. 3 is a relational diagram 300 illustrating several types of information that may be included in a knowledge graph for a pharmaceutical research system and exemplary relations between those types of information. In this example, six types of information are shown with indications of certain relevant relationships and interactions that may be represented in a knowledge graph containing these types of information. The six types of information in this example are chosen to be of particular relevance to pharmaceutical research, and in particular to the analysis of, and prediction of, biochemical properties of proteins and ligands as they relate to disease. Proteins 305 and molecules (ligands) 306 are the primary types of information, as their biochemical relationships and properties determine effects on diseases 303. Genetic information 304 will have an influence on the production of specific proteins 305 and the association with certain diseases 303. Assays 301 will provide information about the quality and quantity relationships of proteins 350 and molecules 306, which provides supporting data for clinical trials 302 and for functional activity relationships with certain diseases 303. Clinical trials 302 provide confirmation of physiological effects and suggestion of biological pathways related to diseases. While this simplified diagram does not purport to show all types of data that may be included or all relationships that may be relevant, it does show certain important types of data and major relevancies that may be included in a knowledge graph to be used for a pharmaceutical research system.

Figure 4:
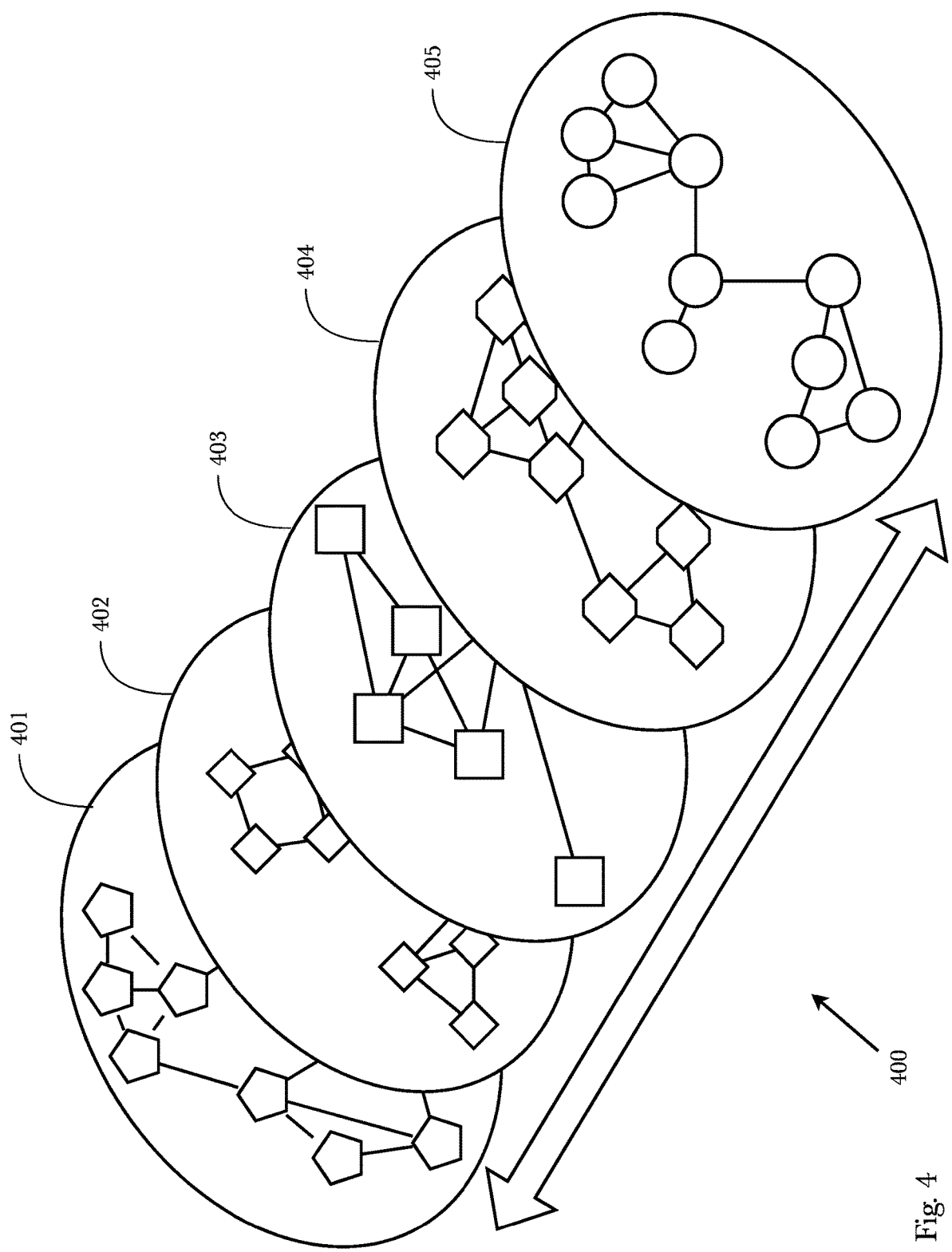
FIG. 4 is a diagram illustrating the conceptual layering of different types of information in a knowledge graph.

FIG. 4 is a diagram illustrating the conceptual layering 400 of different types of information in a knowledge graph. While knowledge graphs are not necessarily constructed in layers, each type of information included in a knowledge graph may be conceived as a layer of information in the knowledge graph and each layer may be analyzed to determine clustering and other relationships within the layer. For example, proceeding with the types of information shown in FIG. 3, the knowledge graph can be conceived of as having layers for clinical trials 401, diseases 402, genetic information 403, assays 404, molecules 405, etc. Relationships such as clustering can be seen at each layer, and can be analyzed separately, if necessary. However, in a knowledge graph, connections between the information at each layer are made and relationships between the information at each layer can be analyzed.

Figure 5:
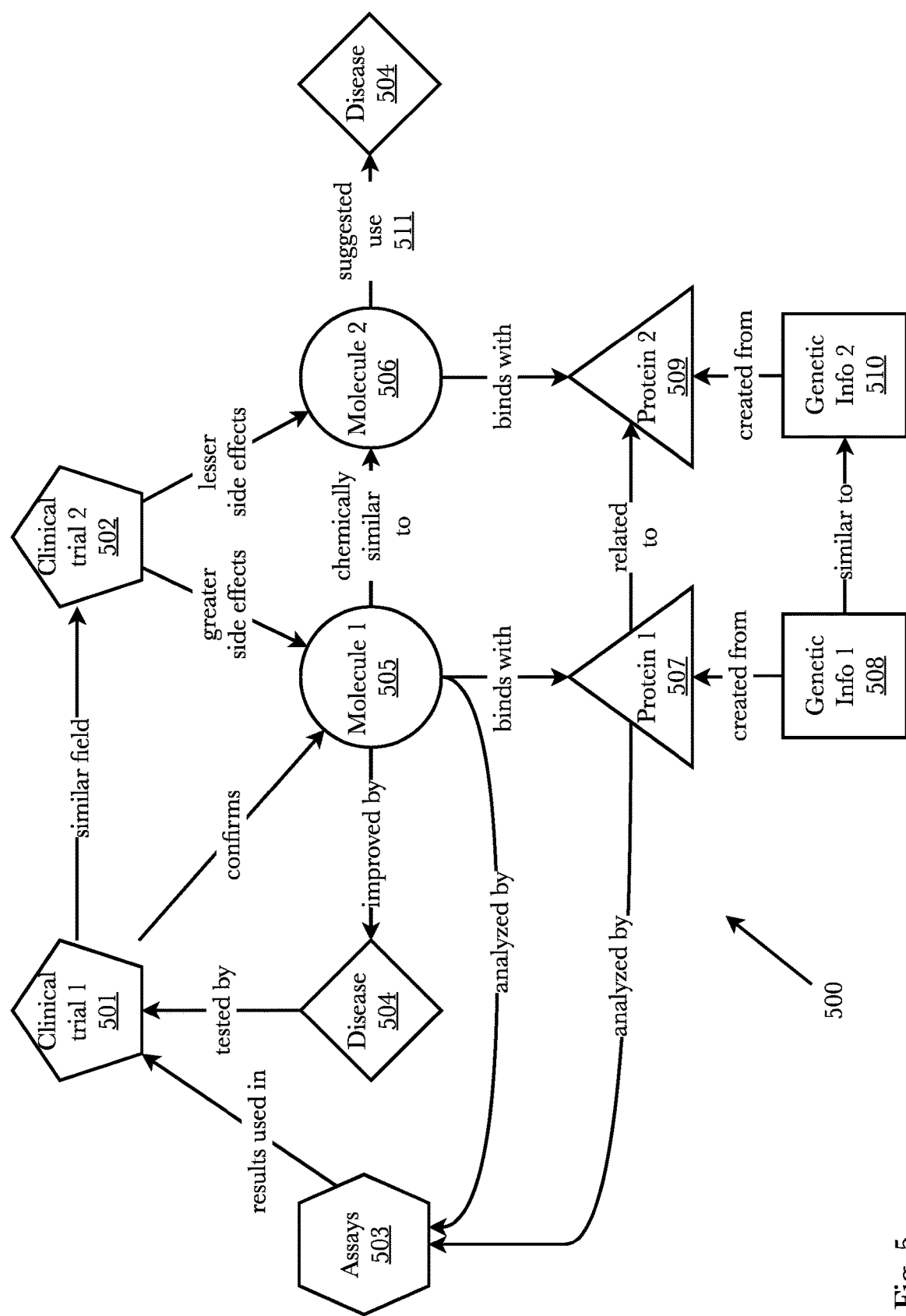
FIG. 5 is a relational diagram illustrating the use of a knowledge graph to predict usefulness of a molecule in treating a disease.

FIG. 5 is a relational diagram illustrating the use of a knowledge graph to predict usefulness of a molecule in treating a disease 500. In this example, a first molecule 505 is known to bind with a first protein 507 which is produced from a first set of genetic information 508. A clinical trial 501 confirmed that the first molecule 505 is effective in treating a disease 504. The clinical trial 501 used information from assays 503 that were performed on the first molecule 505 and the first protein 507. A query has been submitted to the system to identify a second molecule 506 that may also be effective in treating 511 the same disease 504, but with fewer side effects. Using a knowledge graph containing the types of information shown in FIG. 3, and a graph-based machine learning algorithm, the system identifies a second molecule 506 that binds with a second protein 509 which is produced from a second set of genetic information 510. The system determines a number of similarities and relationships between the first molecule 505 and the second molecule 506, including that the first molecule 505 is chemically similar to the second molecule 506, the protein 507 with which the first molecule 505 binds is related to the second protein 509 with which the second molecule 506 binds, and the genetic information (DNA strands) 508 that produces the first protein 507 are similar to the genetic information 510 that produces the second protein 509. Thus, the system determines that the second molecule 506 is likely to have a similar effect on the disease 504 as the first molecule 505. Further, the system identifies a second clinical trial 502 that suggests that the second molecule 506 has lesser side effects than the first molecule 505. As the second molecule 506 meets the query criteria, it is returned as a response to the query.

Figure 6:
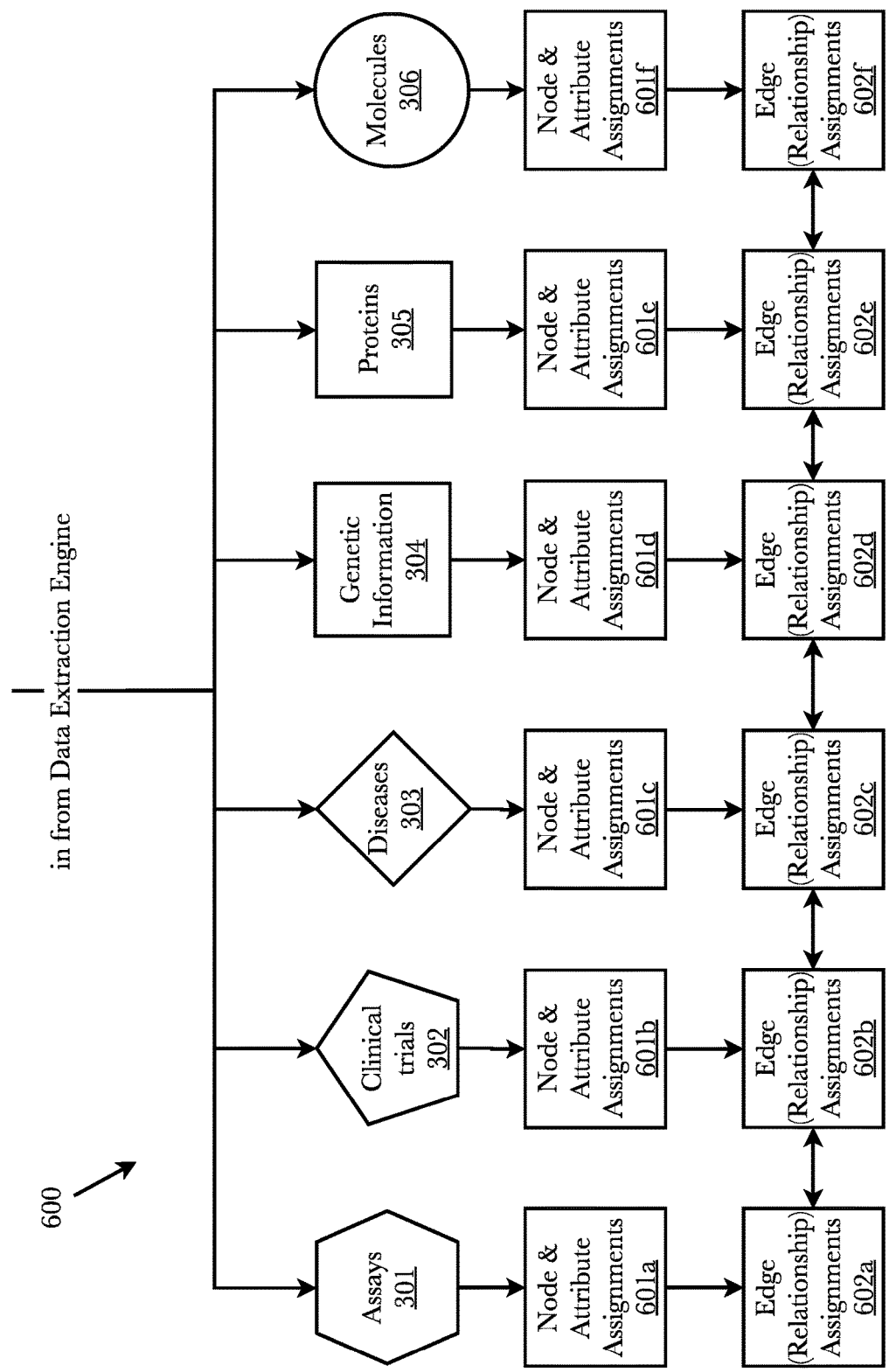
FIG. 6 is a diagram illustrating an exemplary process for combining various types of information into a knowledge graph suitable for a pharmaceutical research system.

FIG. 6 is a diagram illustrating an exemplary process 600 for combining various types of information into a knowledge graph suitable for a pharmaceutical research system. As data is received from a data extraction engine in each of several categories of data (in this example, six categories: assays 301, clinical trials 302, diseases 303, genetic information 304, proteins 305, and molecules 306) nodes are assigned to each entity identified in each category and attributes of the entity are assigned to the node 601a-f. Attributes of the nodes/entity are information describing the characteristics of the nodes/entity. For example, in some embodiments, attributes of nodes related to molecules are in the form of an adjacency matrix which represents the molecule as relationships between the atoms of the molecule. After nodes have been assigned to all identified entities 601a-f, the relationships between entities are assigned, both within the category of knowledge and between all other categories of knowledge 602a-f. As a simple example of the process, assume that a certain molecule 306 is identified during data extraction. A node is created for the molecule and attributes are assigned to the molecule/node in the form of an adjacency matrix representing the molecule as a series of relationships between the atoms of the molecule. Through a series of assays 301 and clinical studies 302, it is known that the molecule binds with a particular protein 305, and is effective in treating a certain disease 303, to which individuals with certain genetic information 304 are susceptible. Nodes are assigned to each of the assays 301, clinical trials 302, diseases 303, proteins 305, and genetic information 304 identified as being associated with the molecule, and edges are established between the nodes reflecting the relevant relationships such as: the molecule binds with the protein, the genetic information is associated with the disease, the clinical trials indicate that the disease is treatable by the molecule, and so on.

Figure 7:
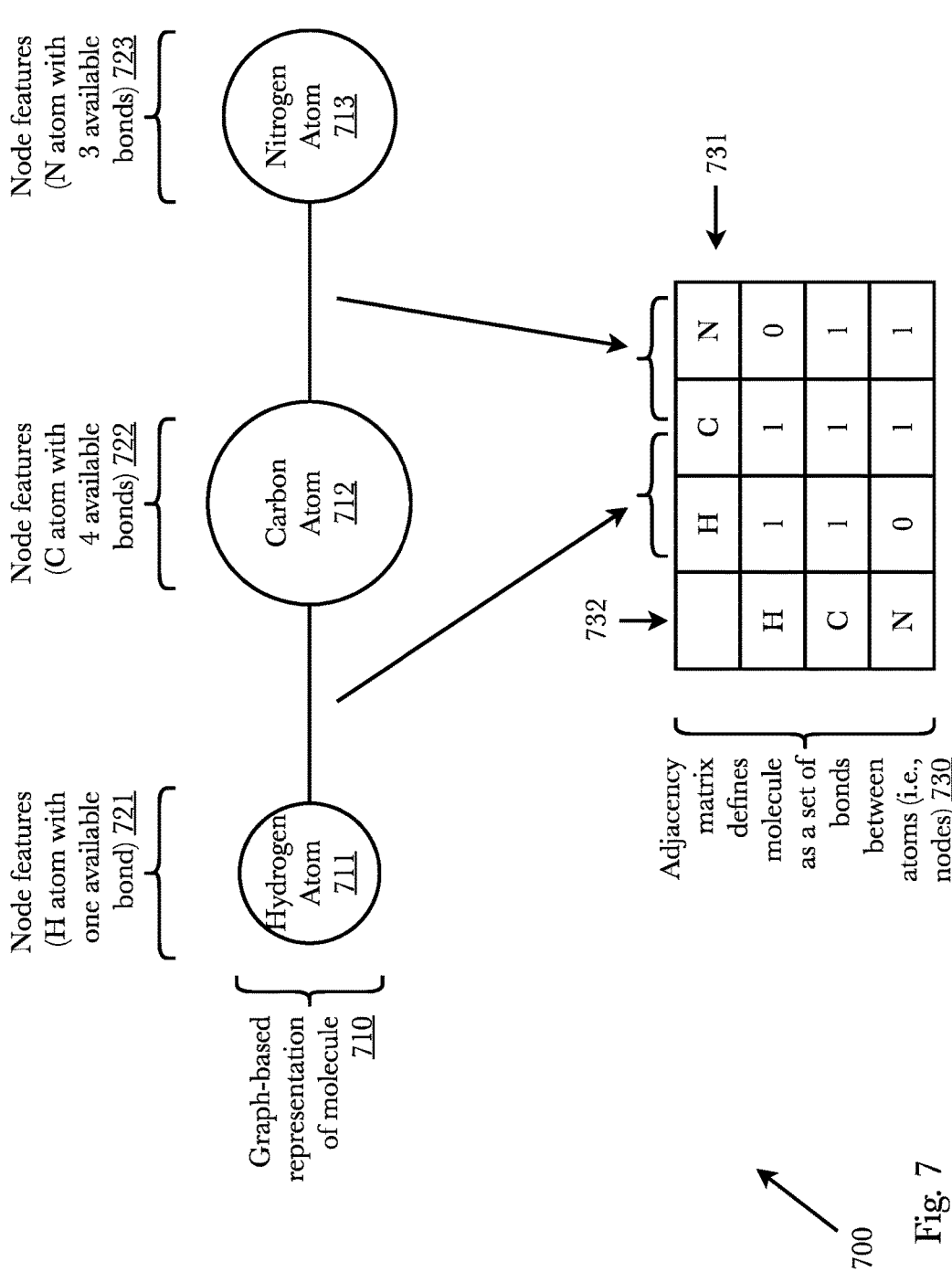
FIG. 7 is a diagram illustrating an exemplary graph-based representation of molecules as simple relationships between atoms using a matrix of adjacencies.

FIG. 7 is a diagram illustrating an exemplary graph-based representation of molecules as simple relationships between atoms using a matrix of adjacencies 700, wherein atoms are represented as nodes and bonds between the atoms are represented as edges. Representation of molecules as a graph is useful because it provides a of molecular structure which can be processed by graph-based machine learning algorithms like GNNs. Further, the graph-based representation of a molecule can be stated in terms of two matrices, one for the node features (e.g., type of atom and its available bonds) and one for the edges (i.e., the bonds between the atoms). The combination of the nodes (atoms) and edges (bonds) represents the molecule.

In this example, a simple hydrogen cyanide molecule is shown as a graph-based representation 710. A hydrogen cyanide molecule consists of three atoms, a hydrogen atom 711, a carbon atom 712, and a nitrogen atom 713. Its standard chemical formula is HCN. Each atom in the molecule is shown as a node of a graph. The hydrogen atom 711 is represented as a node with node features 721 comprising the atom type (hydrogen) and the number of bonds available (one). The carbon atom 712 is represented as a node with node features 722 comprising the atom type (carbon) and the number of bonds available (four). The nitrogen atom 713 is represented as a node with node features 723 comprising the atom type (nitrogen) and the number of bonds available (three). The node features 721, 722, 723 may each be stated in the form of a matrix.

The relationships between the atoms in the molecule are defined by the adjacency matrix 730. The top row of the adjacency matrix 731 shows all of the atoms in the molecule, and the left column of the matrix 732 shows a list of all possible atoms that can be represented by the matrix for a given set of molecules. In this example, the top row 731 and left column 732 contain the same list of atoms, but in cases where multiple molecules are being represented in the system, the left column may contain other atoms not contained in the particular molecule being represented. The matrix shows, for example, that the hydrogen atom 711 is connected to the carbon atom 712 (a "1" at the intersection of the rows and columns for H and C) and that the carbon atom 712 is connected to the nitrogen atom 713 (a "1" at the intersection of the rows and columns for C and N). In this example, each atom is also self-referenced (a "1" at the intersection of the rows and columns for H and H, C and C, and N and N), but in some embodiments, the self-referencing may be eliminated. In some embodiments, the rows and columns may be transposed (not relevant where the matrix is symmetrical, but relevant where it is not).

Figure 8:
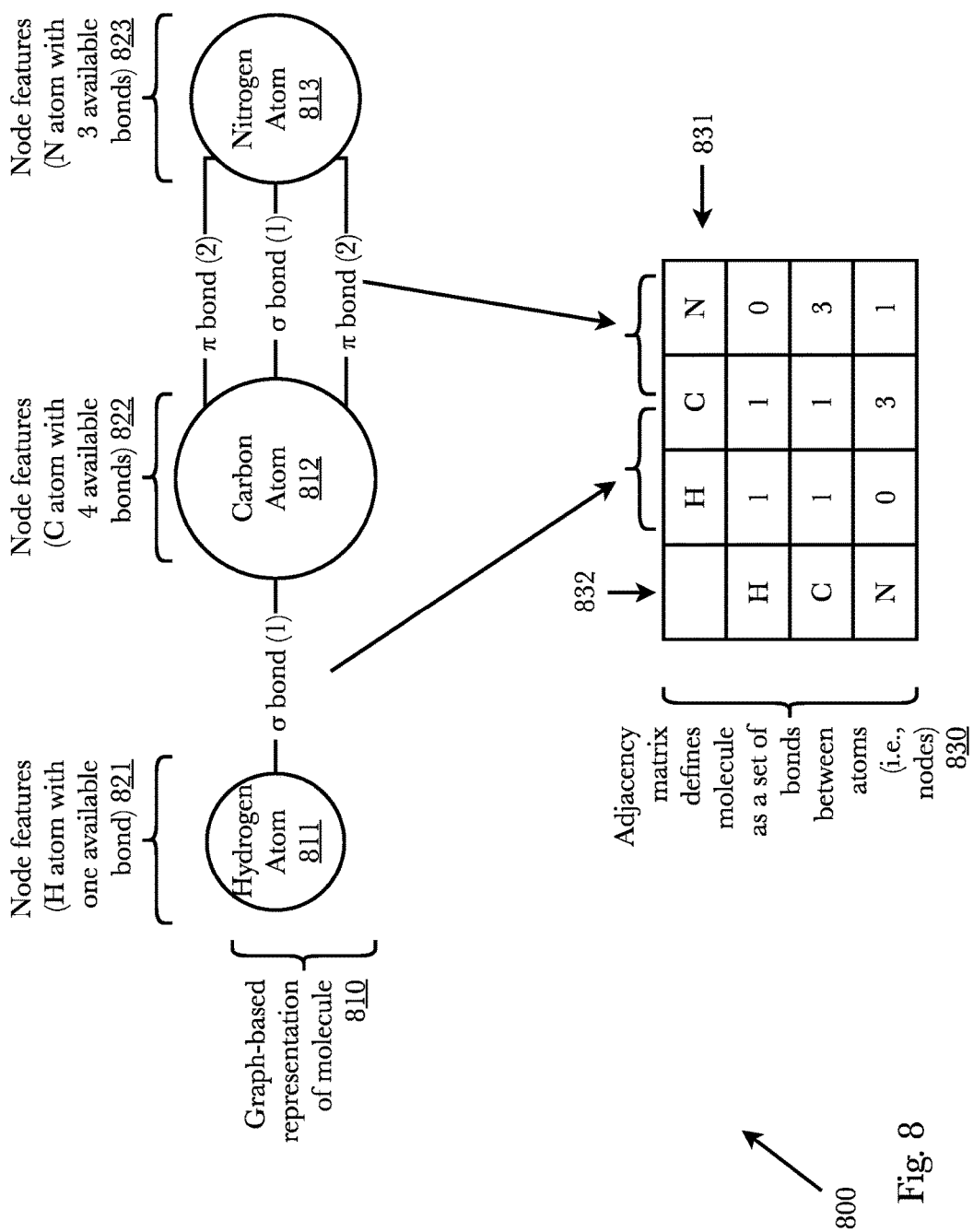
FIG. 8 is a diagram illustrating an exemplary graph-based representation of molecules as relationships between atoms using a matrix of adjacencies wherein the type bonds are distinguished.

FIG. 8 is a diagram illustrating an exemplary graph-based representation of molecules as relationships between atoms using a matrix of adjacencies 800, wherein atoms are represented as nodes and bonds between the atoms are represented as edges, and wherein the type and number of bonds are distinguished. Representation of molecules as a graph is useful because it provides a of molecular structure which can be processed by graph-based machine learning algorithms like GNNs. Further, the graph-based representation of a molecule can be stated in terms of two matrices, one for the node features (e.g., type of atom and its available bonds) and one for the edges (i.e., the bonds between the atoms). The combination of the nodes (atoms) and edges (bonds) represents the molecule.

In this example, a simple hydrogen cyanide molecule is shown as a graph-based representation 810. A hydrogen cyanide molecule consists of three atoms, a hydrogen atom 811, a carbon atom 812, and a nitrogen atom 813. Its standard chemical formula is HCN. Each atom in the molecule is shown as a node of a graph. The hydrogen atom 811 is represented as a node with node features 821 comprising the atom type (hydrogen) and the number of bonds available (one). The carbon atom 812 is represented as a node with node features 822 comprising the atom type (carbon) and the number of bonds available (four). The nitrogen atom 813 is represented as a node with node features 823 comprising the atom type (nitrogen) and the number of bonds available (three). The node features 821, 822, 823 may each be stated in the form of a matrix.

The relationships between the atoms in the molecule are defined by the adjacency matrix 830. The top row of the adjacency matrix 831 shows all of the atoms in the molecule, and the left column of the matrix 832 shows a list of all possible atoms that can be represented by the matrix for a given set of molecules. In this example, the top row 831 and left column 832 contain the same list of atoms, but in cases where multiple molecules are being represented in the system, the left column may contain other atoms not contained in the particular molecule being represented. The matrix shows, for example, that the hydrogen atom 811 is connected to the carbon atom 812 (a "1" at the intersection of the rows and columns for H and C) and that the carbon atom 812 is connected to the nitrogen atom 813 (a "3" at the intersection of the rows and columns for C and N). In this example, the number of bonds between atoms is represented by the digit in the cell of the matrix. For example, a 1 represents a single bond, whereas a 3 represents a triple bond. In this example, each atom is also self-referenced (a "1" at the intersection of the rows and columns for H and H, C and C, and N and N), but in some embodiments, the self-referencing may be eliminated. In some embodiments, the rows and columns may be transposed (not relevant where the matrix is symmetrical, but relevant where it is not).

Figure 9:
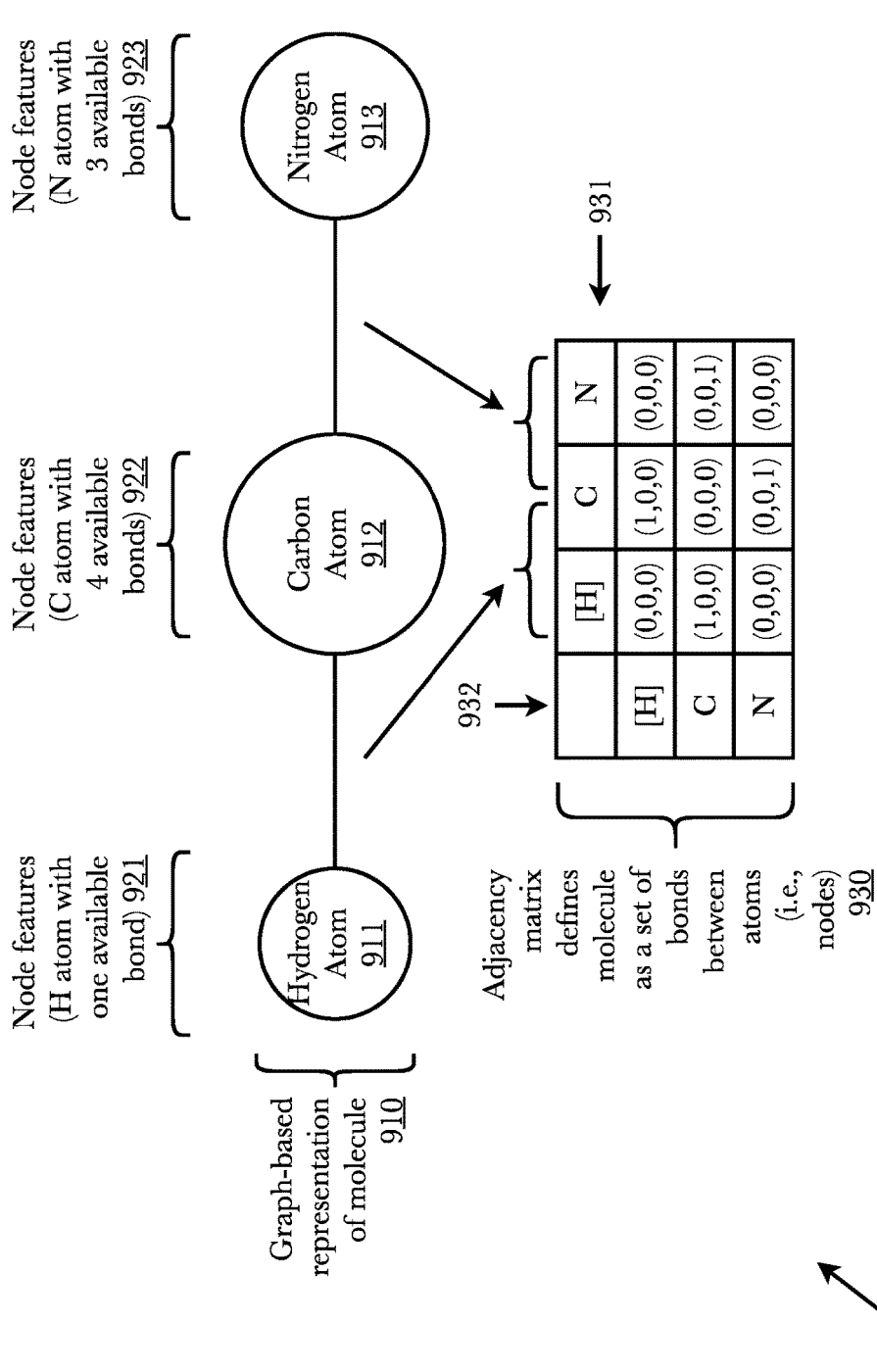
FIG. 9 is a diagram illustrating an exemplary graph-based representation of molecules as relationships between atoms using a matrix of adjacencies using SMILES string encoding and one-hot vectors indicating the types of bonds between atoms.

FIG. 9 is a diagram illustrating an exemplary graph-based representation of molecules as relationships between atoms using a matrix of adjacencies 900, wherein atoms are represented as nodes and bonds between the atoms are represented as edges, and wherein the matrix of adjacencies uses a SMILES string encoding of the molecule and one-hot vector representations of the type of bonds between atoms in the molecule. Representation of molecules as a graph is useful because it provides a of molecular structure which can be processed by graph-based machine learning algorithms like GNNs. Further, the graph-based representation of a molecule can be stated in terms of two matrices, one for the node features (e.g., type of atom and its available bonds) and one for the edges (i.e., the bonds between the atoms). The combination of the nodes (atoms) and edges (bonds) represents the molecule.

In this example, a simple hydrogen cyanide molecule is shown as a graph-based representation 910. A hydrogen cyanide molecule consists of three atoms, a hydrogen atom 911, a carbon atom 912, and a nitrogen atom 913. Its SMILES representation text string is [H]C#N, with the brackets around the H indicating an element other than an organic element, and the # representing a triple bond between the C and N. Each atom in the molecule is shown as a node of a graph. The hydrogen atom 911 is represented as a node with node features 921 comprising the atom type (hydrogen) and the number of bonds available (one). The carbon atom 912 is represented as a node with node features 922 comprising the atom type (carbon) and the number of bonds available (four). The nitrogen atom 913 is represented as a node with node features 923 comprising the atom type (nitrogen) and the number of bonds available (three). The node features 921, 922, 923 may each be stated in the form of a matrix 930.

In this example, the top row 931 and left column 932 contain the same list of atoms, but in cases where multiple molecules are being represented in the system, the left column may contain other atoms not contained in the particular molecule being represented. The matrix shows, for example, that the hydrogen atom 811 is connected to the carbon atom 812 with a single bond (the one-hot vector "(1,0,0)" at the intersection of the rows and columns for H and C) and that the carbon atom 812 is connected to the nitrogen atom 813 with a triple bond (the one-hot vector "(0,0,1)" at the intersection of the rows and columns for C and N). In this example, the number of bonds between atoms is represented by a one-hot vector in the cell of the matrix. For example, a 1 in the first dimension of the vector (1,0,0) represents a single bond, whereas a 1 in the third dimension of the vector (0,0,1) represents a triple bond. In this example, self-referencing of atoms is eliminated, but self-referencing may be implemented in other embodiments, or may be handled by assigning self-referencing at the attention assignment stage. In some embodiments, the rows and columns may be transposed (not relevant where the matrix is symmetrical, but relevant where it is not).

Figure 14:
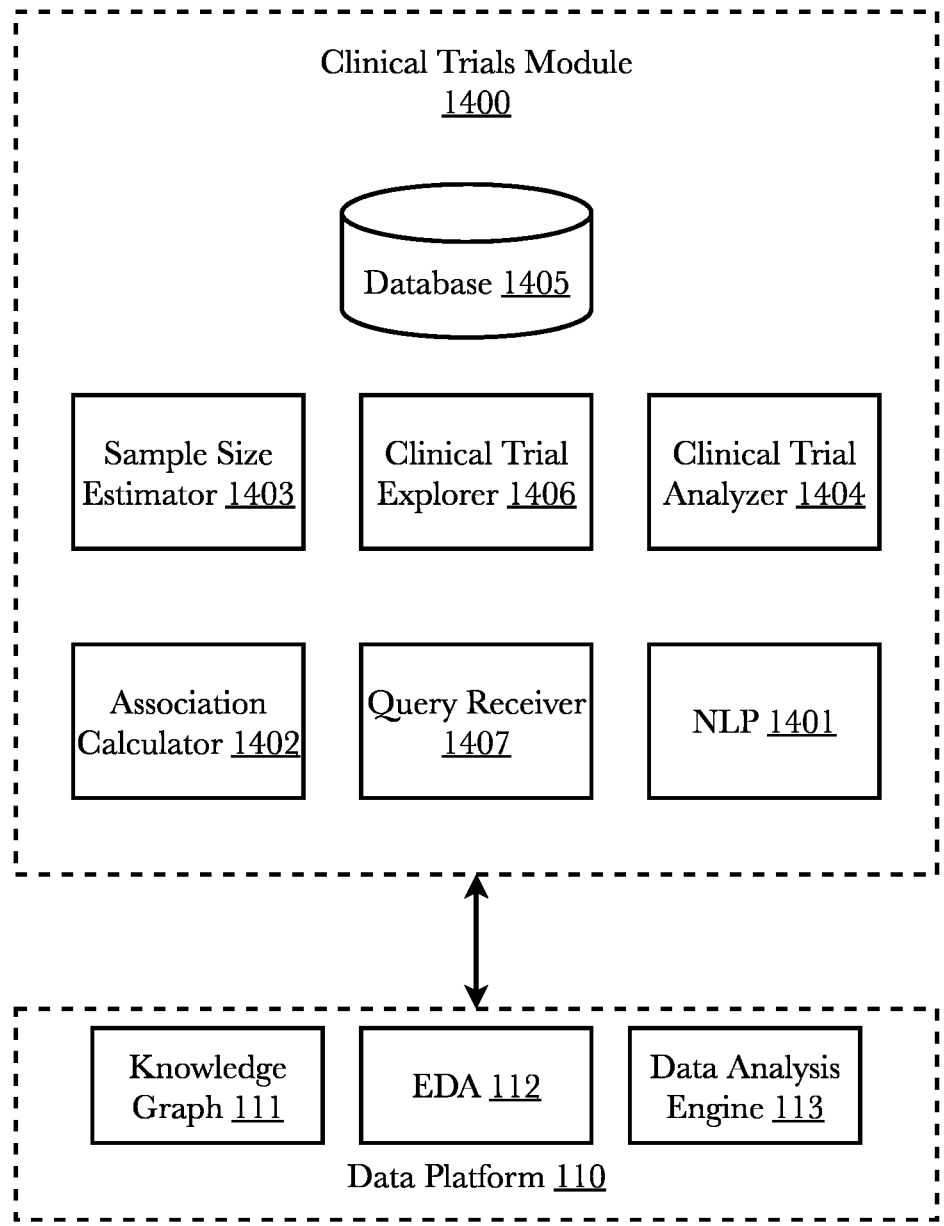
FIG. 14 is a block diagram illustrating an exemplary system architecture for biomarker-outcome prediction and clinical trial exploration, according to an embodiment.

FIG. 14 is a block diagram illustrating an exemplary system architecture for biomarker-outcome prediction and clinical trial exploration 1400, according to an embodiment. The system 1400 leverages the data platform 110 components, knowledge graph 111, exploratory drug analysis (EDA) interface 112, and data analysis engine 113 to provide analytical, discovery, and prediction capabilities based on a large corpus of published clinical trial and assay information. Using the system, users can research a large database of clinical trials by entering queries through the EDA interface 112 which is parsed by a query receiver 1407. Query receiver 1407 receives a query from the EDA 112 and directs the query details to the appropriate end point. One type of query that may be received and processed by the system 1400 is a biomarker search query which causes the system to return a list of papers which link the input biomarker to a plurality of outcomes, forming one or more biomarker-outcome pairs. In this use-case, the query receiver 1407 would send the input biomarker to the NLP—using tool 1401 which would begin parsing all available clinical trial publications to identify and then return all publications that mention the input biomarker. Additionally, biomarkers may be empirically linked to some outcome. The association calculator 1402 utilizes the NLP—using tool 1401 to calculate the co-occurrence of biomarker-outcome pairs to generate an association rank which may represent the biological or medical relationship between biomarker and outcome. Calculated association scores may be persisted in a database 1405. Another type of query that may be received and processed by the system 1400 is a sample size query. A sample size query may consist of input terms which describe the goal, methodology, and design of a potential clinical trial in order to provide context for the sample size estimator 1403 to calculate a sample size. Sample size estimator 1403 may use prior information sampled from similar historical clinical trial data based on input terms.

When the data platform 110 ingests a clinical trial publication it may be sent to a natural language processing pipeline 1401 which scrapes a publication for information that pertains to custom fields of a standard clinical trial data model. Once a publication has been fully scraped, the standard data model is persisted to a database 1405 and the information contained within the standard data model is added to the knowledge graph 111. A clinical trial explorer 1406 may pull information about each clinical trial from its standard data model as well as from a subset of the knowledge graph 111 in order to create a navigable user interface for clinical trial exploration. In one embodiment, the clinical trial explorer 1406 may create a global map of research centers which have published medical literature pertaining to clinical trials, assays, or research studies using the geolocation data scraped during the data ingestion process. The global map would allow a user to navigate and explore clinical trials associated with each research center. For example, a research center may be denoted with a star on a map and a user could hover over the star to get a quick snapshot of the research center, the snapshot may include information such as, but not limited, the research center name, total number of publications, research field (i.e., drug research, genetic research, etc.), and most recent publication. Clicking on the star would take the user to a separate page populated with the abstracts of each published paper and a link that directs the user to the original paper. The separate page may also include for each paper a list of any biomarkers and biomarker-outcome pairs discussed within each paper. In other embodiments, the clinical trial explorer 1406 may facilitate clinical trial exploration via a navigable graph interface.

The clinical trial analyzer 1404 may utilize the data analysis engine 113 and knowledge graph 111 to provide explanatory capabilities that provide deeper context between a biomarker and an outcome. The knowledge graph 111 contains a massive amount of data spanning categories such as diseases, proteins, molecules, assays, clinical trials, and genetic information all collated from a large plurality of medical literature and research databases which may be used to provide more insight into biomarker-outcome relationships. A clinical trial may provide a relational link between a biomarker and an outcome, as an example consider the biomarker chloride: an increased chloride level in hypochloremia is associated with decreased mortality in patients with severe sepsis or septic shock. In this example the biomarker is associated with the adverse event (outcome) of mortality and with the outcome sepsis/septic shock. The clinical trial analyzer 1404 may scan the knowledge graph 111 for sepsis or septic shock and then find what biological process associated with sepsis. It is known that sepsis occurs when chemicals released in the bloodstream to fight an infection trigger inflammation throughout the body which can cause a host of changes that can damage various organ systems. For example, the analyzer 1404 may be able to identify the molecular profile of the chemicals released into the blood stream and then make a connection between the molecules and chloride that provide a richer context between chloride and sepsis. In this way the biomarker-outcome prediction and clinical trial exploration system 1400 may provide explanatory capabilities to add deeper understanding between a biomarker and outcome.

Detailed Description of Exemplary Aspects

Figure 10:
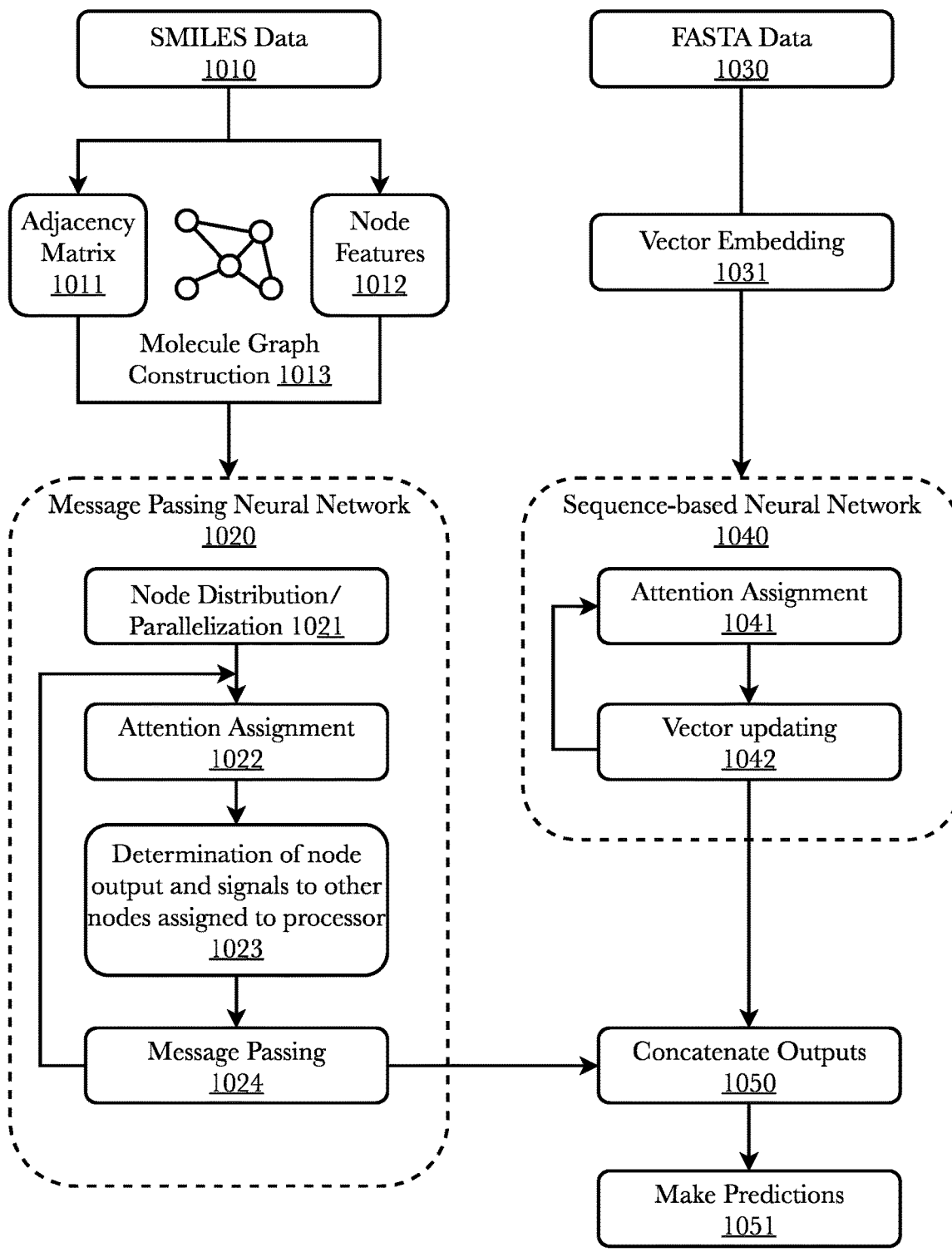
FIG. 10 is a diagram illustrating an exemplary architecture for prediction of molecule bioactivity using concatenation of outputs from a graph-based neural network which analyzes molecule structure and a sequence-based neural network which analyzes protein structure.

FIG. 10 is a diagram illustrating an exemplary architecture for prediction of molecule bioactivity using concatenation of outputs from a graph-based neural network which analyzes molecules and their known or suspected bioactivities with proteins and a sequence-based neural network which analyzes protein segments and their known or suspected bioactivities with molecules. In this architecture, in a first neural network processing stream, SMILES data 1010 for a plurality of molecules is transformed at a molecule graph construction stage 1013 into a graph-based representation wherein each molecule is represented as a graph comprising nodes and edges, wherein each node represents an atom and each edge represents a connection between atoms of the molecule. Each node represents the atom as node features comprising an atom type and a number of bonds available for that atom. The node features are represented as a node features matrix 1012. The molecule, then, is represented as nodes (atoms) connected by edges (bonds), and is specified as an adjacency matrix 1011 showing which nodes (atoms) are connected to which other nodes (atoms).

At the training stage, the adjacency matrices 1011 and node features matrices 1012 for many molecules are input into the MPNN 1020 along with vector representations of known or suspected bioactivity interactions of each molecule with certain proteins. Based on the training data, the MPNN 1020 learns the characteristics of molecules and proteins that allow interactions and what the bioactivity associated with those interactions is. At the analysis stage, a target molecule is input into the MPNN 1020, and the output of the MPNN 102 is a vector representation of that molecule's likely interactions with proteins and the likely bioactivity of those interactions.

Once the molecule graph construction 1013 is completed, the node features matrices 1012 and adjacency matrices 1011 are passed to a message passing neural network (MPNN) 1020, wherein the processing is parallelized by distributing groups 1021 nodes of the graph amongst a plurality of processors (or threads) for processing. Each processor (or thread) performs attention assignment 1022 on each node, increasing or decreasing the strength of its relationships with other nodes, and outputs of the node and signals to other neighboring nodes 1023 (i.e., nodes connected by edges) based on those attention assignments are determined. Messages are passed 1024 between neighboring nodes based on the outputs and signals, and each node is updated with the information passed to it. Messages can be passed between processors and/or threads as necessary to update all nodes. In some embodiments, this message passing (also called aggregation) process is accomplished by performing matrix multiplication of the array of node states by the adjacency matrix to sum the value of all neighbors or divide each column in the matrix by the sum of that column to get the mean of neighboring node states. This process may be repeated an arbitrary number of times. Once processing by the MPNN is complete, its results are sent for concatenation 1050 with the results from a second neural network, in this case a long short term memory neural network 1040 which analyzes protein structure.

In a second processing stream, FASTA data 1030 is converted to high-dimensional vectors 1031 representing the amino acid structure of proteins. The vectors are processed by a long short term memory (LSTM) neural network 1040 which performs one or more iterations of attention assignment 1041 and vector updating 1042. The attention assignment 1041 of the LSTM 1040 operates in the same way as that of the MPNN 1020, although the coding implementation will be different. At the vector updating stage 1042, the vectors comprising each cell of the LSTM 1040 are updated based on the attention assignment 1041. This process may be repeated an arbitrary number of times. Once processing by the LSTM 1040 is complete, its results are sent for concatenation 1050 with the results from the first processing stream, in this case the MPNN 1020.

Concatenation of the outputs 1050 from two different types of neural networks (here an MPNN 1020 and an LSTM 1040) determines which molecule structures and protein structures are compatible, allowing for prediction of bioactivity 1051 based on known or suspected similarities with other molecules and proteins.

Figure 11A:
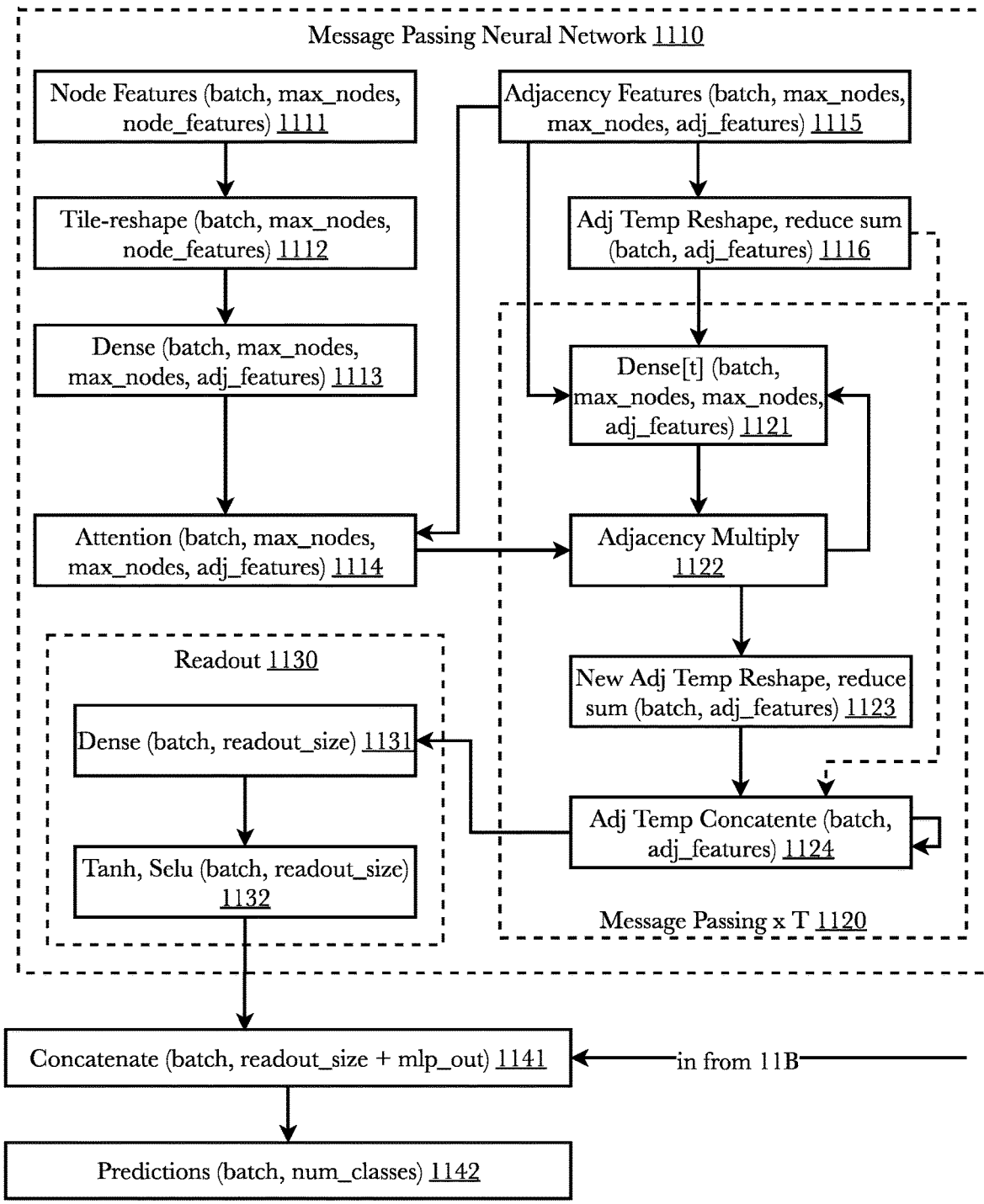
FIGS. 11A and 11B illustrates an exemplary implementation of an architecture for prediction of molecule bioactivity using concatenation of outputs from a graph-based neural network which analyzes molecule structure and a sequence-based neural network which analyzes protein structure.
Figure 11B:
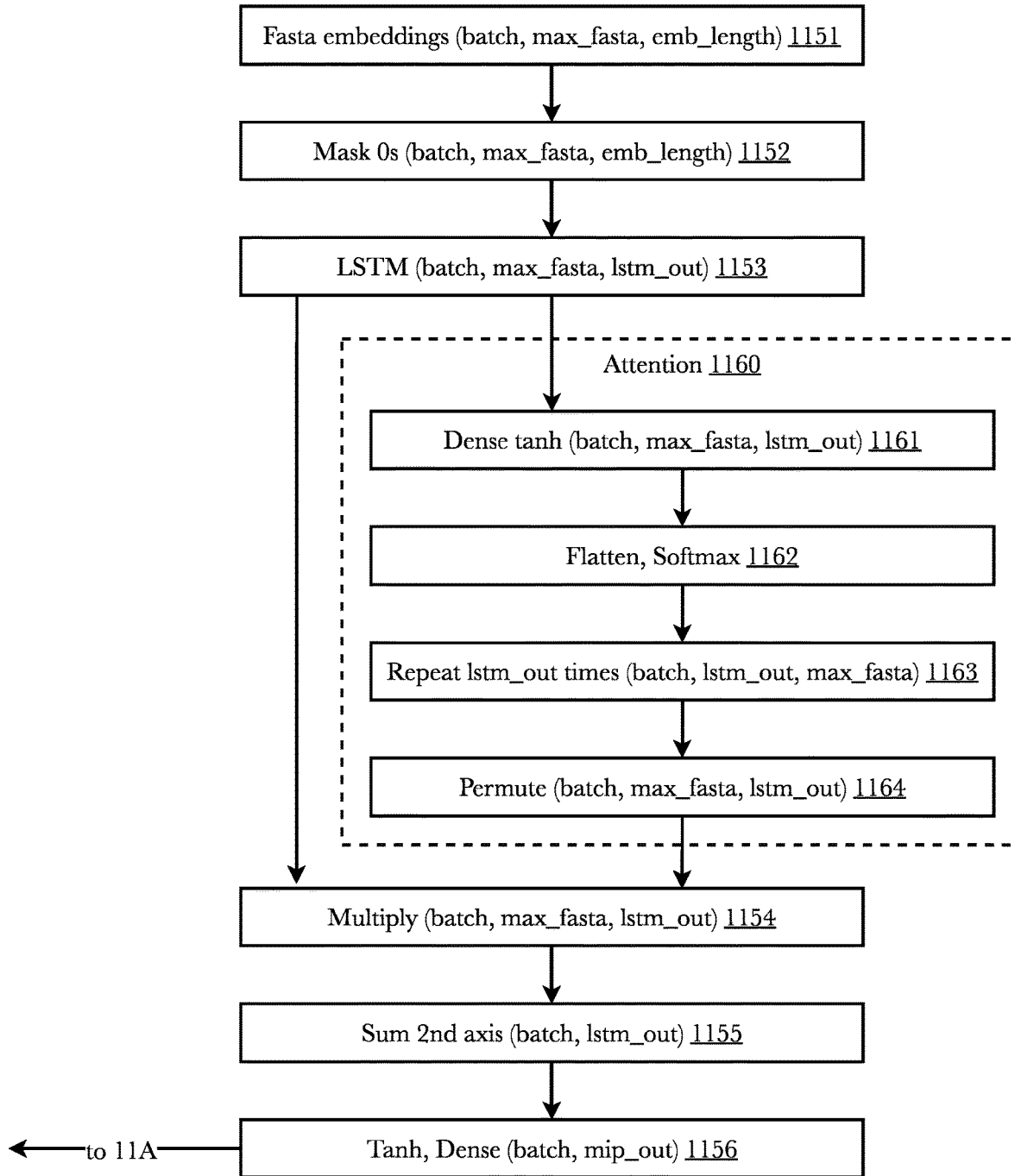

FIGS. 11A and 11B illustrate an exemplary implementation of the architecture for prediction of molecule bioactivity using concatenation of outputs from a graph-based neural network which analyzes molecule structure and a sequence-based neural network which analyzes protein structure. In this example, details regarding a particular implementation of the general architecture shown in FIG. 10 are described.

As shown in FIG. 11A, node features 1111 are received for processing. A reshaping process 1112 may be performed which to conform the dimensionality of the inputs to the dimensionality required for processing by the MPNN. A dense function 1113 is performed to map each node in the previous layer of the neural network to every node in the next layer. Attention is then assigned 1114 using the adjacency matrix contained in the node. The adjacency features (the adjacency matrix) 1115 are simultaneously reshaped 1116 to conform the dimensionality of the inputs to the dimensionality required for processing by the MPNN.

At this stage, a message passing operation 1120 is performed, comprising the steps of performing a dense function 1121 (used only on the first message pass) to map each node in the previous layer of the neural network to every node in the next layer, matrix multiplication of the adjacencies 1122, reshaping of the new adjacencies 1123, and where the message passing operation has been parallelized among multiple processors or threads, concatenating the outputs of the various processors or threads 1124.

Subsequently, a readout operation 1130 is performed comprising performance of a dense function 1131 and implementation of an activation function 1132 such as tan h, selu, etc. to normalize the outputs to a certain range. In this embodiment, the readout operation 1130 is performed only at the first message pass of the MPNN 1110.

As shown in FIG. 11B, FASTA data is converted to high-dimensional vectors 1151, which may then be masked 1152 to conform the vectors to the fixed input length required by the LSTM 1153. The LSTM 1153 then processes the vectors using an attention mechanism 1160 comprising the steps of performing a dense function 1161 to map each node in the previous layer of the neural network to every node in the next layer, performing a softmax function 1162 to assign probabilities to each node just before the output layer. The process is repeated a number of times which may be configured by a parameter 1163. Where permutation invariance is an issue (i.e., where changes in the order of inputs yield changes in the outputs), permutations may be applied to the inputs 1164 to ensure that differences in outputs due to differences in inputs are incorporated.

After attention has been assigned 1160, the vectors in the cells of the LSTM 1153 are multiplied 1154, summed 1155, and a dense function 1156 is again applied to map each node in the previous layer of the neural network to every node in the next layer, and the outputs of the LSTM 1153 are sent for concatenation 1141 with the outputs of the MPNN 1110, after which predictions can be made 1142.

Figure 12:
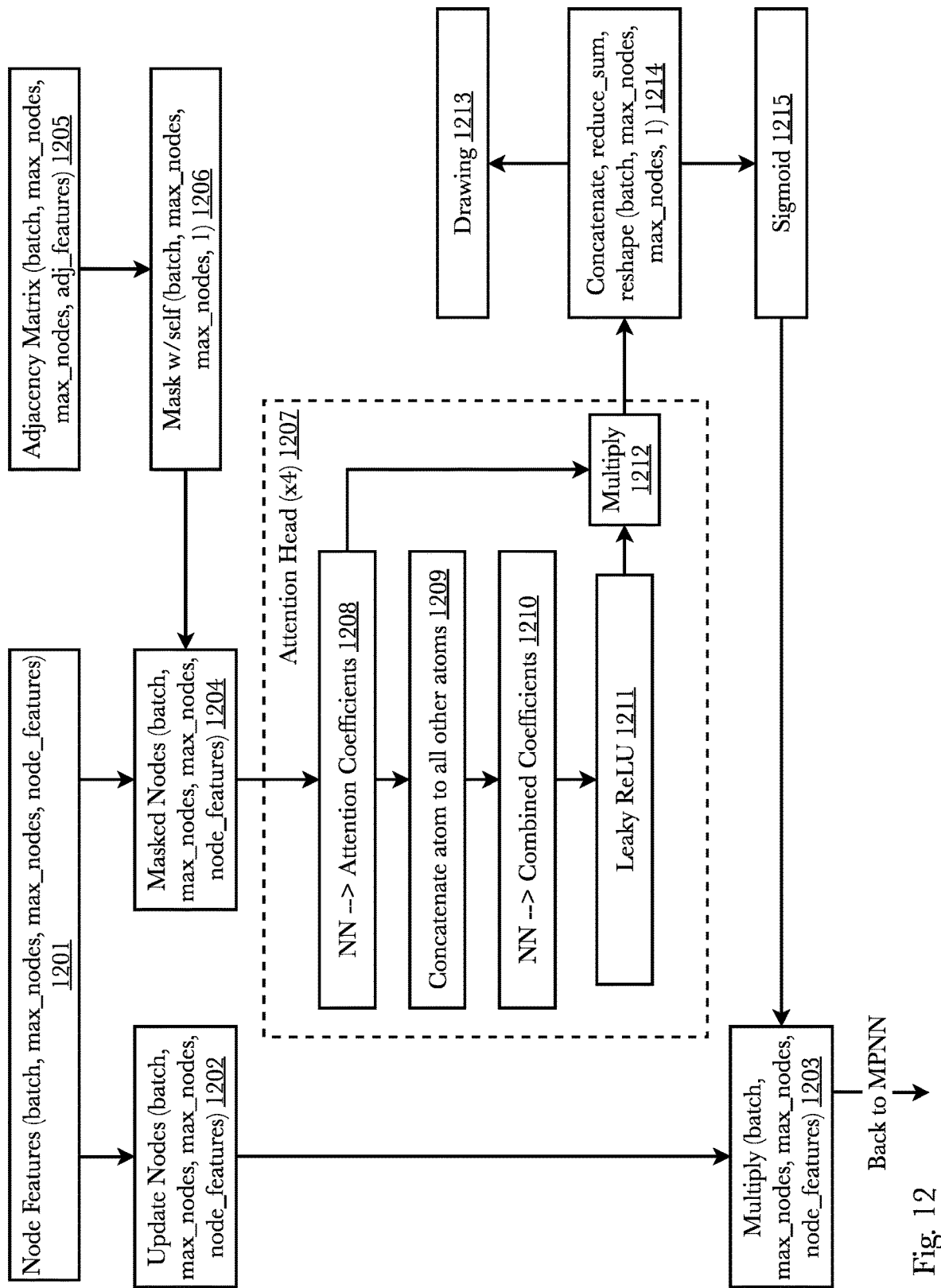
FIG. 12 illustrates an exemplary implementation of the molecule attention assignment aspect of an architecture for prediction of molecule bioactivity using concatenation of outputs from a graph-based neural network which analyzes molecule structure and a sequence-based neural network which analyzes protein structure.

FIG. 12 illustrates an exemplary implementation of an attention assignment aspect of an architecture for prediction of molecule bioactivity using concatenation of outputs from a graph-based neural network which analyzes molecule structure and a sequence-based neural network which analyzes protein structure. In this example, details regarding a particular implementation of the attention assignment blocks shown in FIG. 10 are described. The particular implementation of this example involves a multi-head attention mechanism.

As node features 1201 are received for processing, they are updated 1202 and sent for later multiplication 1203 with the outputs of the multiple attention heads 1207. Simultaneously, the nodes are masked 1204 to conform their lengths to a fixed input length required by the attention heads 1207. The adjacency matrix 1205 associated with (or contained in) in each node is also masked 1206 to conform it to a fixed length and sent along with the node features to the multi-head attention mechanism 1207.

The multi-head attention mechanism 1207 comprises the steps of assigning attention coefficients 1208, concatenating all atoms to all other atoms 1209 (as represented in the adjacency matrix), combining the coefficients 1210, performing a Leaky ReLU 1211 function to assign probabilities to each node just before the output layer, and performing matrix multiplication 1212 on the resulting matrices.

The outputs of the multi-head attention mechanism 1207 are then concatenated 1214, and optionally sent to a drawing program for display of the outputs in graphical form 1213. A sigmoid function 1215 is performed on the concatenated outputs 1214 to normalize the outputs to a certain range. The updated node features 1202 are then multiplied 1203 with the outputs of the multi-head attention mechanism 1207, and sent back to the MPNN.

Figure 13:
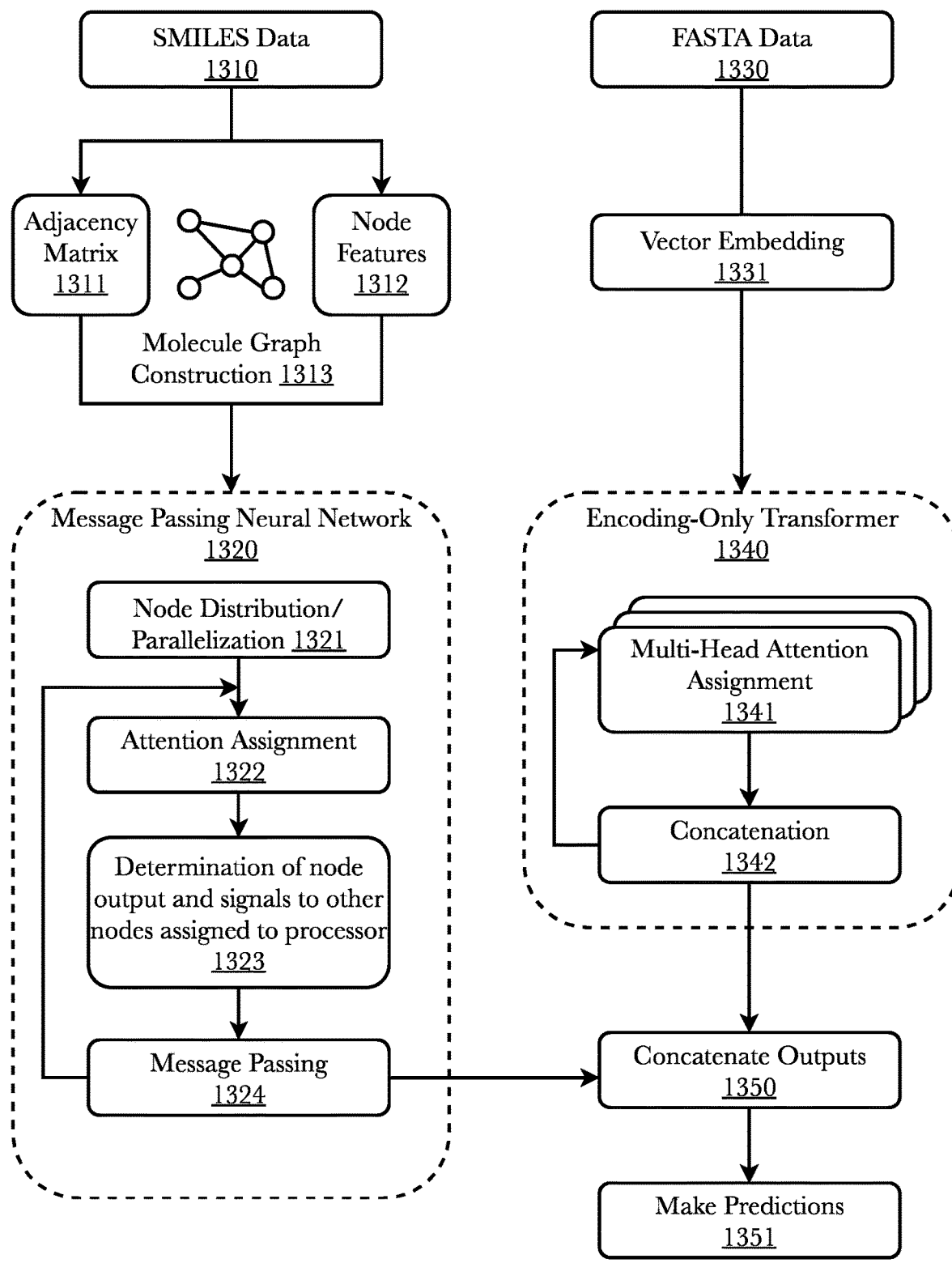
FIG. 13 is a diagram illustrating an exemplary architecture for prediction of molecule bioactivity using concatenation of outputs from a graph-based neural network and an attention-based transformer.

FIG. 13 is a diagram illustrating an exemplary architecture for prediction of molecule bioactivity using concatenation of outputs from a graph-based neural network which analyzes molecules and their known or suspected bioactivities with proteins and a sequence-based neural network which analyzes protein segments and their known or suspected bioactivities with molecules. In this architecture, in a first neural network processing stream, SMILES data 1310 for a plurality of molecules is transformed at a molecule graph construction stage 1313 into a graph-based representation wherein each molecule is represented as a graph comprising nodes and edges, wherein each node represents an atom and each edge represents a connection between atoms of the molecule. Each node represents the atom as node features comprising an atom type and a number of bonds available for that atom. The node features are represented as a node features matrix 1312. The molecule, then, is represented as nodes (atoms) connected by edges (bonds), and is specified as an adjacency matrix 1311 showing which nodes (atoms) are connected to which other nodes (atoms).

At the training stage, the adjacency matrices 1311 and node features matrices 1312 for many molecules are input into the MPNN 1320 along with vector representations of known or suspected bioactivity interactions of each molecule with certain proteins. Based on the training data, the MPNN 1320 learns the characteristics of molecules and proteins that allow interactions and what the bioactivity associated with those interactions is. At the analysis stage, a target molecule is input into the MPNN 1320, and the output of the MPNN 1320 is a vector representation of that molecule's likely interactions with proteins and the likely bioactivity of those interactions.

Once the molecule graph construction 1013 is completed, the node features matrices 1012 and adjacency matrices 1011 are passed to a message passing neural network (MPNN) 1020, wherein the processing is parallelized by distributing groups 1321 nodes of the graph amongst a plurality of processors (or threads) for processing. Each processor (or thread) performs attention assignment 1322 on each node, increasing or decreasing the strength of its relationships with other nodes, and outputs of the node and signals to other neighboring nodes 1323 (i.e., nodes connected by edges) based on those attention assignments are determined. Messages are passed 1324 between neighboring nodes based on the outputs and signals, and each node is updated with the information passed to it. Messages can be passed between processors and/or threads as necessary to update all nodes. In some embodiments, this message passing (also called aggregation) process is accomplished by performing matrix multiplication of the array of node states by the adjacency matrix to sum the value of all neighbors or divide each column in the matrix by the sum of that column to get the mean of neighboring node states. This process may be repeated an arbitrary number of times. Once processing by the MPNN is complete, its results are sent for concatenation 1350 with the results from a second machine learning algorithm, in this case an encoding-only transformer 1340.

In a second processing stream, FASTA data 1330 is converted to high-dimensional vectors 1331 representing the chemical structure of molecules. The vectors are processed by an encoding-only transformer 1340 which performs one or more iterations of multi-head attention assignment 1341 and concatenation 1342. Once processing by the encoding-only transformer 1340 is complete, its results are sent for concatenation 1350 with the results from the neural network, in this case the MPNN 1320.

Concatenation of the outputs 1350 from two different types of neural networks (here an MPNN 1320 and an LSTM 1340) determines which molecule structures and protein structures are compatible, allowing for prediction of bioactivity 1351 based the information learned by the neural networks from the training data.

Figure 15:
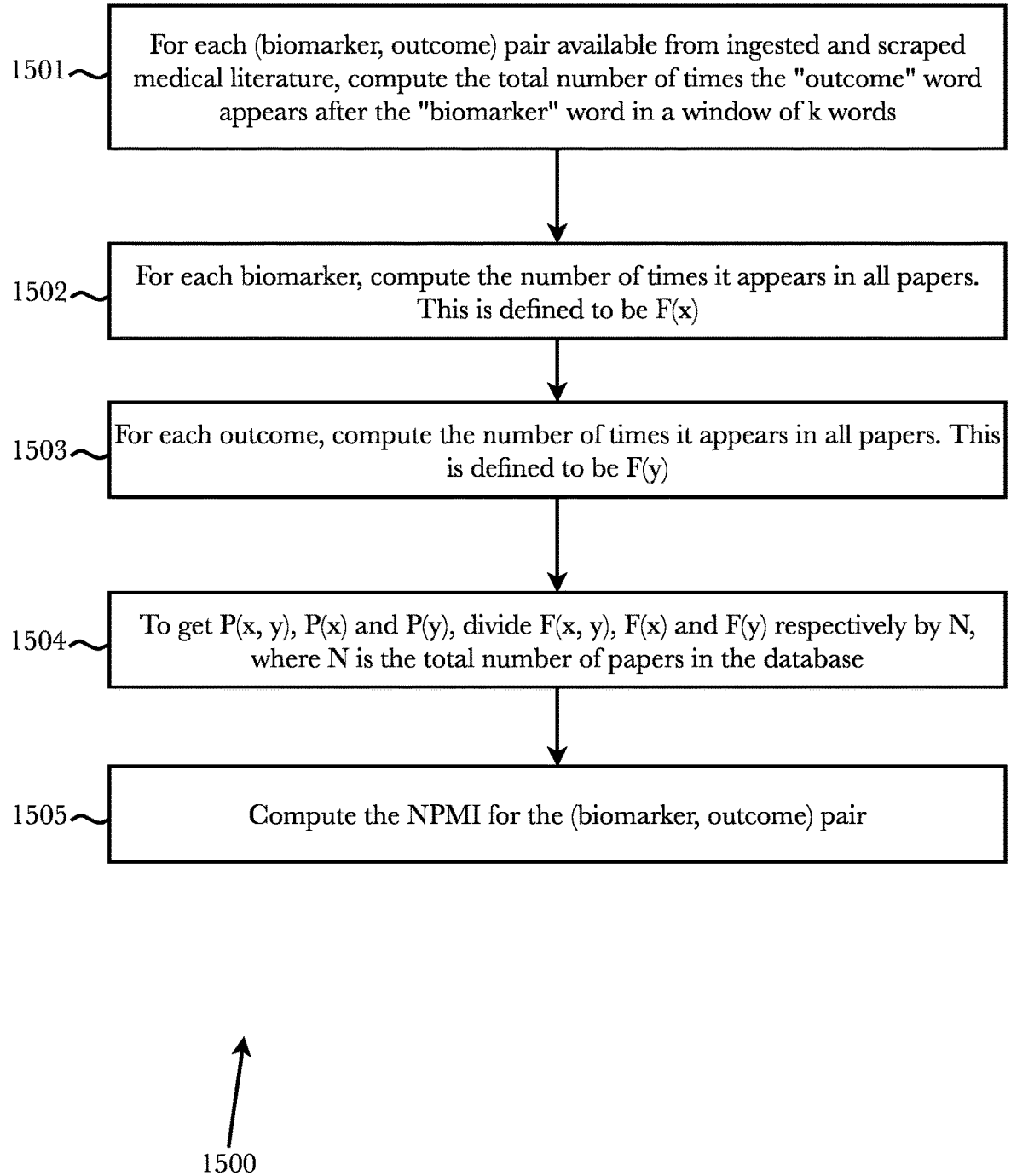
FIG. 15 is a flow diagram illustrating an exemplary method for calculating the association score for a biomarker-outcome bigram, according to one embodiment.

FIG. 15 is a flow diagram illustrating an exemplary method 1500 for calculating the association score for a biomarker-outcome pair, according to one embodiment. The biomarker-outcome prediction and medical literature exploration system xx may compute an association score for a given biomarker-outcome pair. In a preferred embodiment, the association score may be computed using a normalized pointwise mutual information (NPMI) function to measure the co-occurrence of the "biomarker" word and the "outcome" word. Given two points (words) x and y, the pointwise mutual information (PMI) is defined as:

$$PMI(x, y) = \log_2 \frac{P(x, y)}{P(x)P(y)}$$

If there is really an association between a biomarker and an outcome, the probability of observing the (biomarker, outcome) pair in one group of words will be much higher than what is expected by chance. The normalized pointwise information is:

$$NPMI(x, y) = \frac{PMI(x, y)}{-\log_2 P(x, y)}$$

Normalizing the PMI function reduces the error that can occur with less frequently occurring words and also produces a bounded answer that is more readily meaningful from an analysis perspective. The calculated association score represents how often, as referenced in medical literature data, a biomarker and a particular outcome occur together in a medically relevant context.

As a first step, the system may for each biomarker pair available from ingested and scraped medical literature, compute the total number of times the "outcome" word appears after the "biomarker" word in a window of k words 1501. Often k is set to five words, but the size of the window may be adjusted both up and down as needed. The total number computed may be defined as the function F(biomarker, outcome) or synonymously F(x, y). A window of words is selected because, oftentimes in medical literature, a biomarker may be connected to an outcome via verbs or phrases that indicate a relationship. The biomarker-outcome pair may be, for example, Albumin-liver disease which may be associated with each other as described by medical literature such as "The best understood mechanism of chronic hypoalbuminemia is the decreased albumin synthesis observed in liver disease". From that example it can be seen that both the biomarker (Albumin) and outcome (liver disease) are associated with each other, but that the word pair does not necessarily occur consecutively one after the other, therefore it is necessary to create a window of words in which to capture the co-occurrence of the word pair.

Then, for each biomarker, the system computes the number of times it appears in all papers and define this number to be F(x) 1502. The data platform contains over thirty million medical research papers which pass through a natural language processing (NLP) pipeline which extracts relevant information including, but not limited to, proteins, genetic information, diseases, molecules, biomarkers, clinical trials, assays, and biomarkers. Additionally, for each outcome, compute the number of times it appears in all papers and define this number to be F(y) 1503. The next step is to derive P(x, y), P(x) and P(y) by dividing F(x, y), F(x) and F(y) respectively by N, where N is the total number of papers in the data platform database 1504. Once these values have been derived, the system is able to compute the NMPI for the (biomarker, outcome) pair 1505. This value is the association rank between the pair and may be persisted to a database and viewed when making a biomarker query to the EDA 112.

Figure 16:
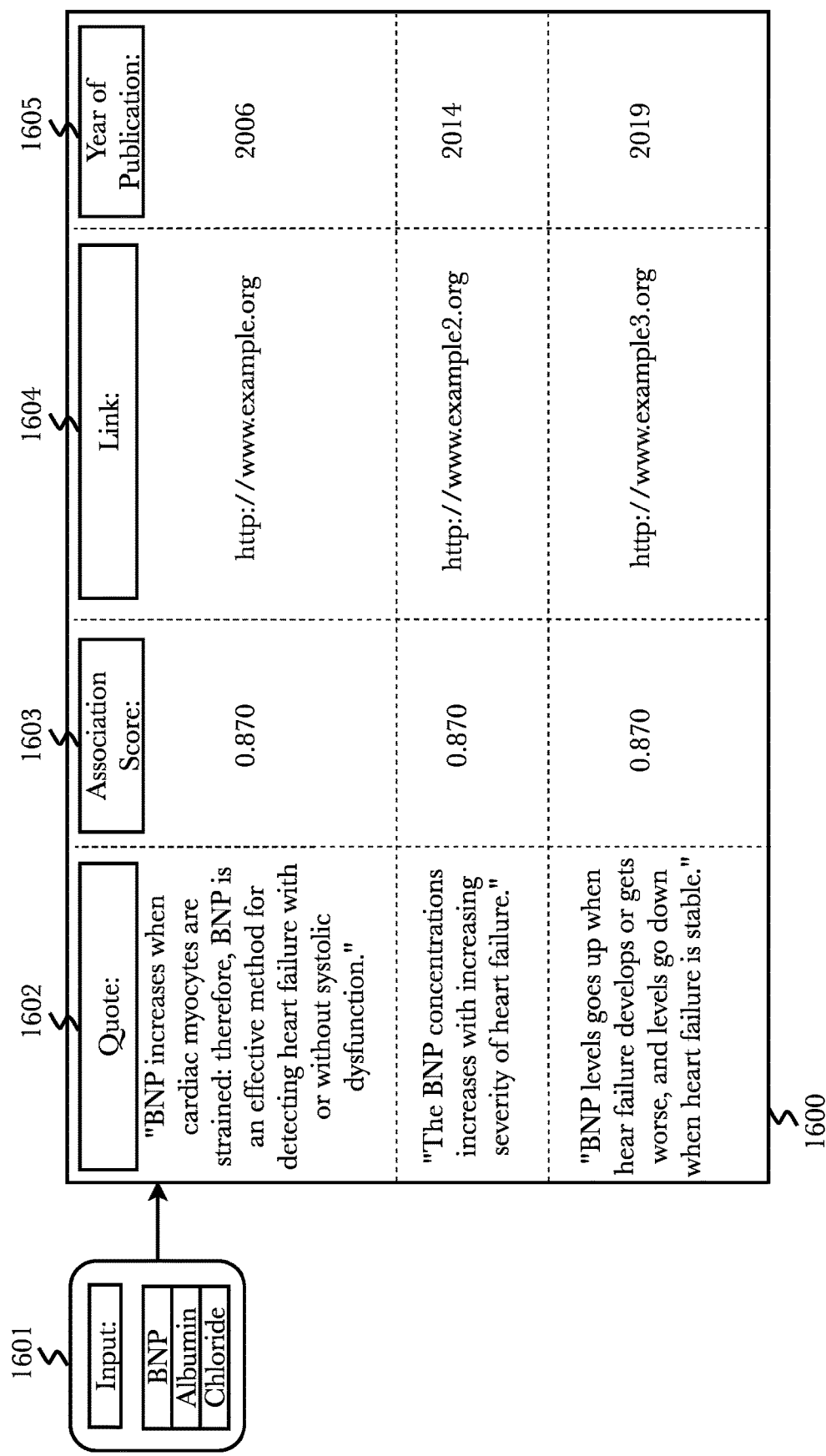
FIG. 16 is a diagram illustrating an exemplary interactive exploration tool, according to an embodiment.

FIG. 16 is a diagram illustrating an exemplary output list 1600 generated from an input list of biomarkers to be measured using the biomarker-outcome prediction and clinical trial exploration system, according to an embodiment. A system user (e.g., pharmaceutical company, contract research organization, etc.) who is interested in running a clinical trial, may input a list 1601 of biomarkers that will be measured during screening or continuously throughout a clinical trial for each patient. The NLP 1401 may be utilized so that for each biomarker the system can return a list of papers that contain associations between that biomarker and side effects, diseases, adverse events, etc.

In this exemplary diagram a biomarker input list 1601 contains three biomarkers of interest: B-type natriuretic peptide (BNP), Albumin, and chloride levels in blood. The biomarker-outcome prediction and medical literature exploration system 1400 returns an output list 1600 of papers that show the associations between the input list biomarkers and some diseases or side effects. In one embodiment, the output list may comprise a quote section 1602 which displays the relevant sentence where the biomarker and outcome are associated, an association score section 1603 which displays the computed association score between an input biomarker and the associated outcome found within the displayed quote, a link section 1604 which provides a clickable web-link where the paper the quote was sourced from can be found in its entirety, and a section that displays the year of publication 1605 of the listed output papers.

In this example diagram, an abridged version of the output list for only the BNP input biomarker is shown, but in practice a biomarker may be associated with hundreds of outcomes and the output list may accordingly span hundreds of papers. Additionally, the output list for each input biomarker would also be displayed, but for simplicity sake the output lists for the other two biomarkers (Albumin and Chloride) have been left out of this exemplary diagram. A pharmaceutical company or research entity may use this system when designing a clinical trial where one or more biomarkers may be measured in order to quickly collate the most relevant and recent information about how each biomarker is related to each outcome.

Figure 17:
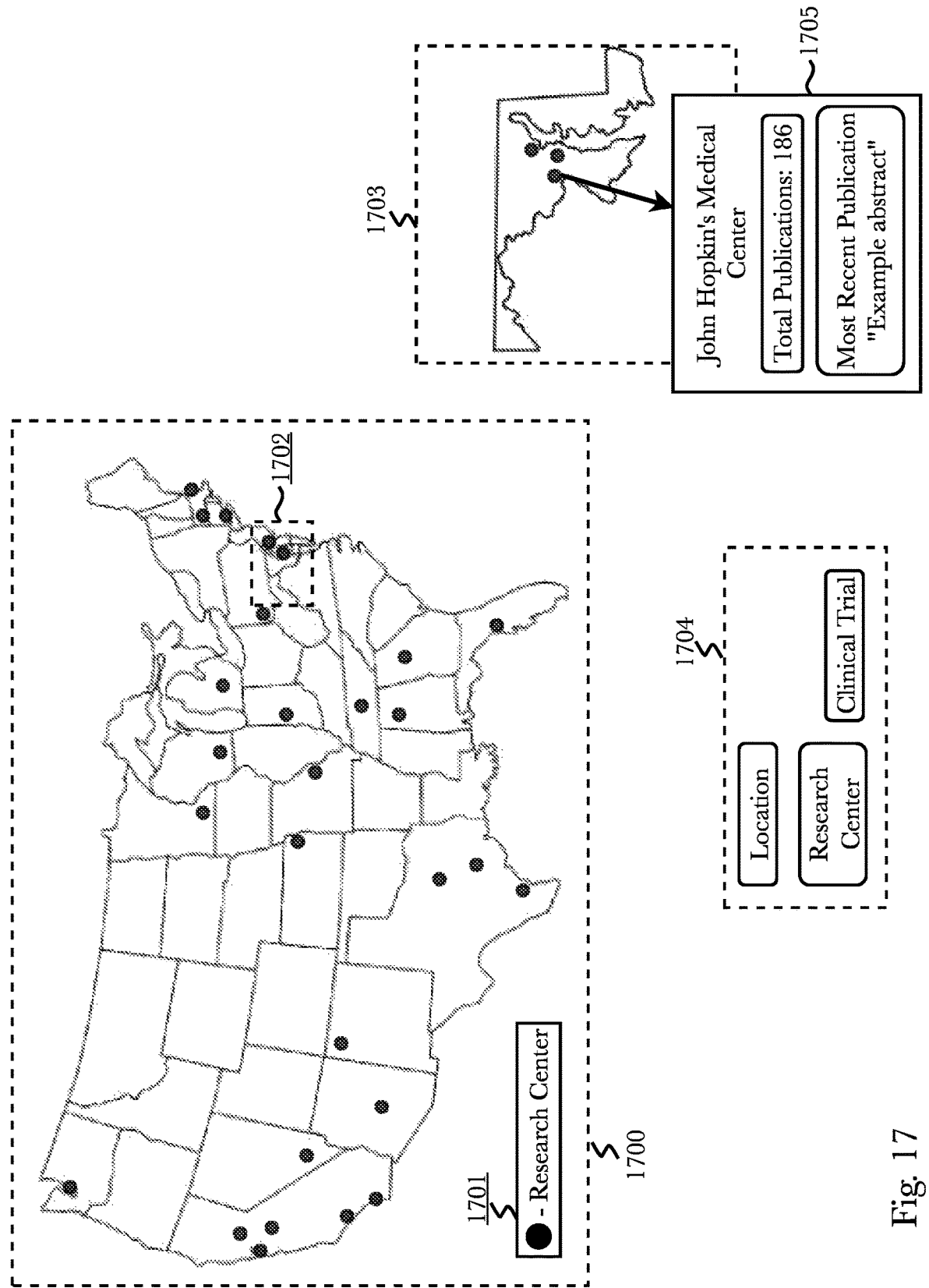
FIG. 17 is a diagram illustrating an exemplary output list generated from an input list of biomarkers to be measured, according to an embodiment.

FIG. 17 is a diagram illustrating an exemplary interactive exploration tool in the form of a map 1700 as created by the clinical trial explorer 1406, according to an embodiment. The clinical trial prediction and exploration system 1400 may facilitate exploration of the historical clinical trial, assay, or research paper data by providing a navigable interactive global map of research centers. The clinical trial prediction and exploration system utilizes the geolocation data extracted during data ingestion to provide an interactive map 1700 populated with the locations of research centers and the biomedical literature associated with each research center. Each black dot on the map represents a research center that has published biomedical literature, as described by the legend 1701. The global map is fully navigable in that it allows a user to scroll across the entire map, zoom in or out at a desired location, and click on research centers to view publication originating from there. In a zoomed out view, a user may drag and highlight a subsection 1702 of the graph to provide a zoomed in view 1703 of the selected area.

Additionally, the map may provide one or more of filters 1704 that may allow a user to narrow or broaden the scope of the map. Filters may include, for example, locational filters (e.g., by continent, country, state, city, etc.), research center filters which allow a user to specify which research centers to display, clinical trial filters that allow a user to view clinical trials related to a specific aspect of interest (i.e., disease, biomarker, outcome, adverse event, etc.). A user may hover a computer mouse icon over a research center to cause a research center snapshot 1705 to appear which may provide information including, but not limited to, the research center name, total number of publications produced by the research center, and the abstract of the most recently published paper originating from the research center. Clicking on a research center will cause a new page to be loaded populated with a list of all published papers originating from that research center as well as any available or derived statistics regarding clinical trial data.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific aspects, at least some of the features or functionalities of the various aspects disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some aspects, at least some of the features or functionalities of the various aspects disclosed herein may be implemented in one or more virtualized computing environments (e.g., network computing clouds, virtual machines hosted on one or more physical computing machines, or other appropriate virtual environments).

Figure 18:
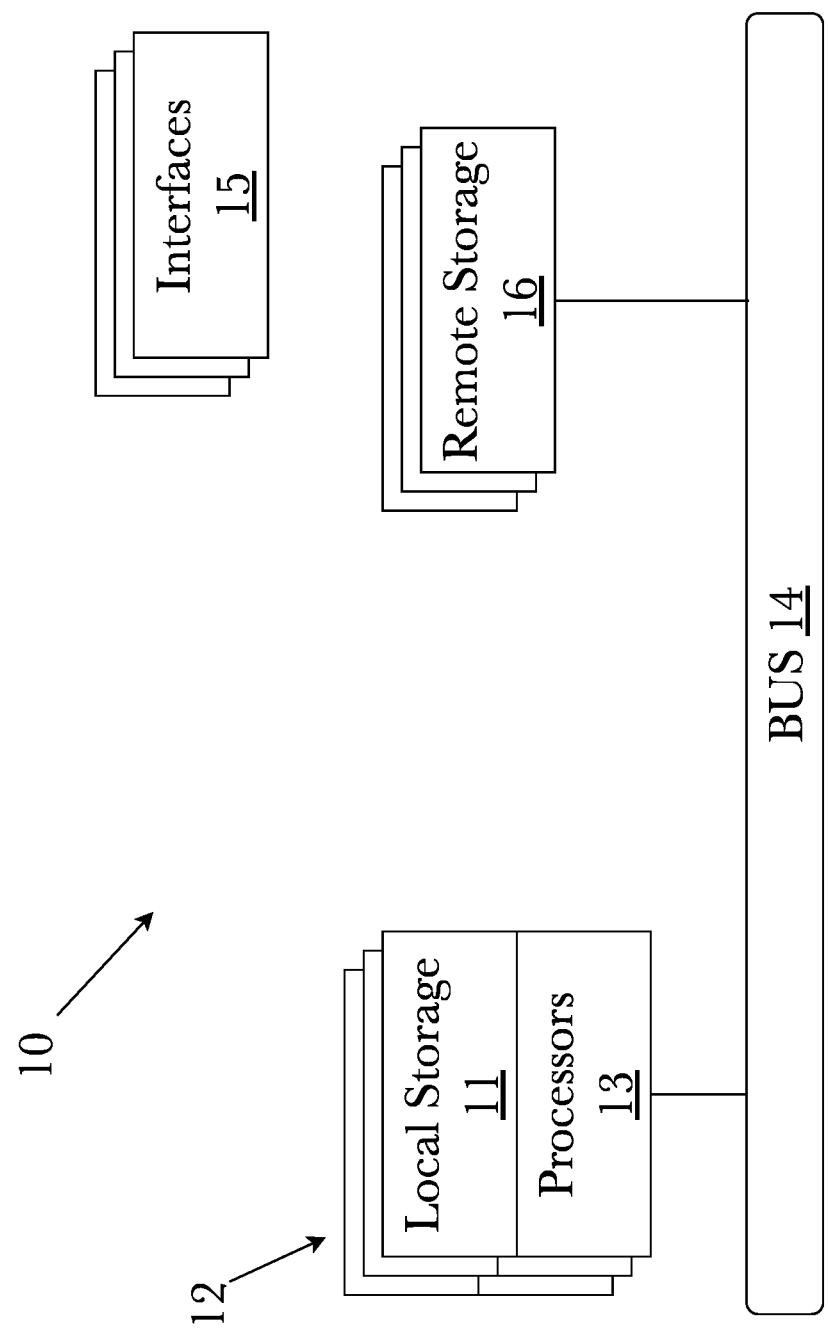
FIG. 18 is a block diagram illustrating an exemplary hardware architecture of a computing device.

Referring now to FIG. 18, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some aspects, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/N hardware interfaces) and, in some instances, volatile and/or non-volatile memory (e.g., RAM).

Although the system shown in FIG. 18 illustrates one specific architecture for a computing device 10 for implementing one or more of the aspects described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, a single processor 13 handles communications as well as routing computations, while in other aspects a separate dedicated communications processor may be provided. In various aspects, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the aspects described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device aspects may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 19:
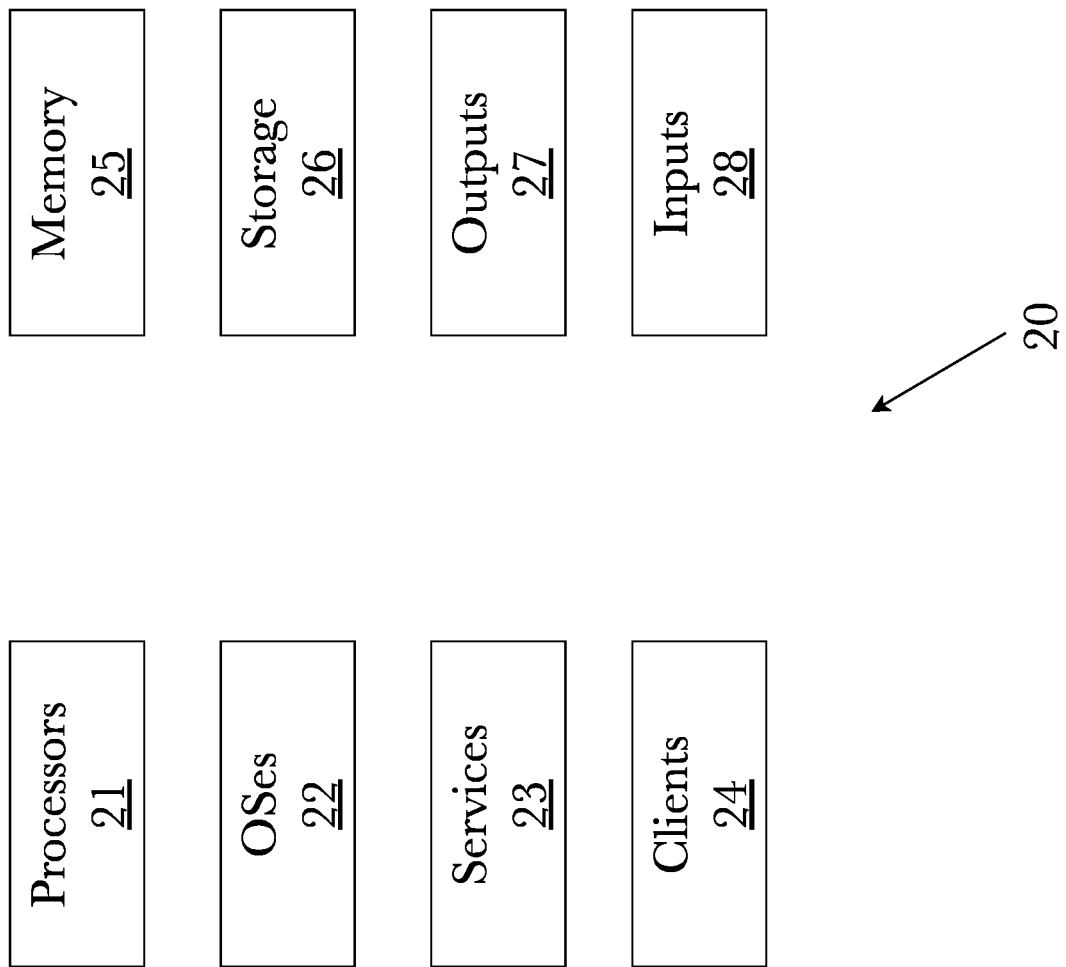
FIG. 19 is a block diagram illustrating an exemplary logical architecture for a client device.

In some aspects, systems may be implemented on a standalone computing system. Referring now to FIG. 19, there is shown a block diagram depicting a typical exemplary architecture of one or more aspects or components thereof on a standalone computing system. Computing device 20 includes processors 21 that may run software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 18). Examples of storage devices 26 include flash memory, magnetic hard drive, CD-ROM, and/or the like.

Figure 20:
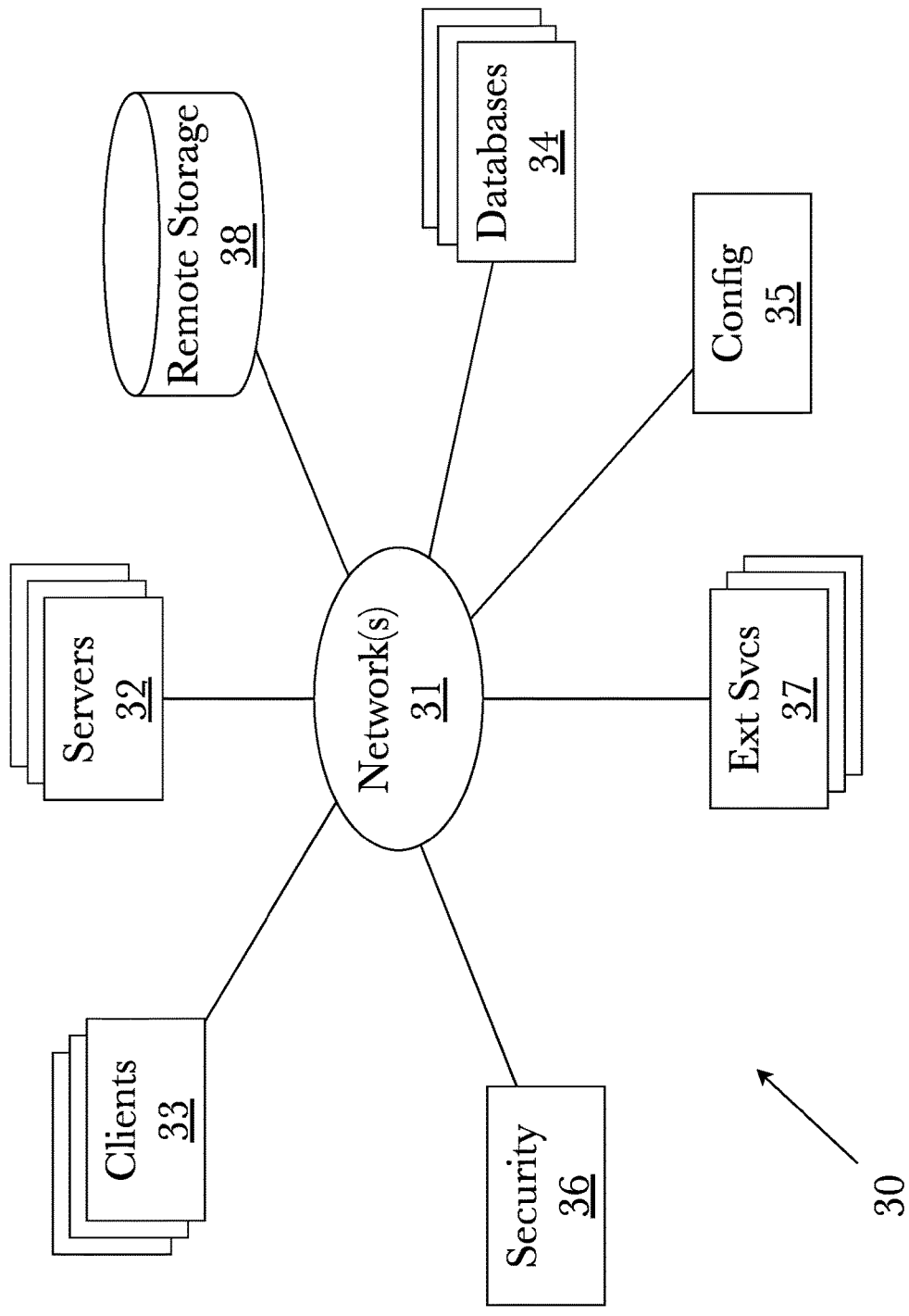
FIG. 20 is a block diagram showing an exemplary architectural arrangement of clients, servers, and external services.

In some aspects, systems may be implemented on a distributed computing network, such as one having any number of clients and/or servers. Referring now to FIG. 20, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 19. In addition, any number of servers 32 may be provided for handling requests received from one or more clients 33. Clients 33 and servers 32 may communicate with one another via one or more electronic networks 31, which may be in various aspects any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some aspects, servers 32 may call external services 37 when needed to obtain additional information, or to refer to additional data concerning a particular call. Communications with external services 37 may take place, for example, via one or more networks 31. In various aspects, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises. In addition to local storage on servers 32, remote storage 38 may be accessible through the network(s) 31.

In some aspects, clients 33 or servers 32 (or both) may make use of one or more specialized services or appliances that may be deployed locally or remotely across one or more networks 31. For example, one or more databases 34 in either local or remote storage 38 may be used or referred to by one or more aspects. It should be understood by one having ordinary skill in the art that databases in storage 34 may be arranged in a wide variety of architectures and using a wide variety of data access and manipulation means. For example, in various aspects one or more databases in storage 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some aspects, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some aspects may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with aspects without limitation, unless a specific security 36 or configuration system 35 or approach is specifically required by the description of any specific aspect.

Figure 21:
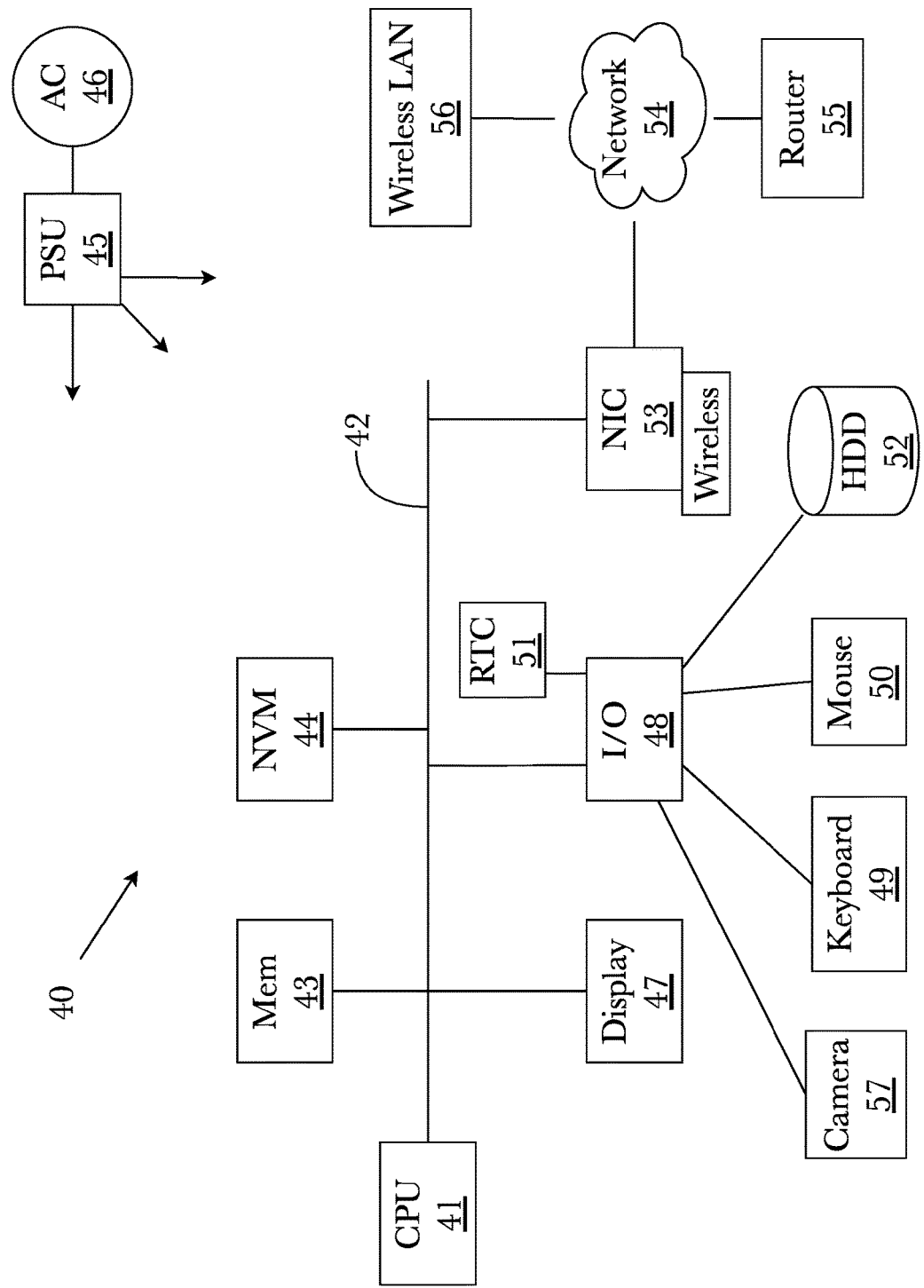
FIG. 21 is another block diagram illustrating an exemplary hardware architecture of a computing device.

FIG. 21 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to peripherals such as a keyboard 49, pointing device 50, hard disk 52, real-time clock 51, a camera 57, and other peripheral devices. NIC 53 connects to network 54, which may be the Internet or a local network, which local network may or may not have connections to the Internet. The system may be connected to other computing devices through the network via a router 55, wireless local area network 56, or any other network connection. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various aspects, functionality for implementing systems or methods of various aspects may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various aspects described above. Accordingly, the present invention is defined by the claims and their equivalents.

What is claimed is:

1. A system for calculating an association score between a biomarker and some outcome, comprising:
   a computing device comprising a memory and a processor;
   a database comprising clinical trial publications;
   an automated text mining tool comprising at first plurality of programming instructions stored in the memory and operating on the processor of, wherein the first plurality of programming instructions, when operating on the processor, causes the computing device to:
     receive a clinical trial publication;
     scrape the clinical trial publications for biomarker and outcome word pairs; and
     compute the total number of times the outcome word appears after the biomarker word in a window of words for all clinical trial publications;
   an association calculator comprising at first plurality of programming instructions stored in the memory and operating on the processor of, wherein the first plurality of programming instructions, when operating on the processor, causes the computing device to:
     compute the probability of occurrence for each biomarker by dividing the computed total number of times each biomarker appears in all papers by the total number of publications in the database;
     compute the probability of occurrence for each outcome by dividing the computed total number of times each outcome appears in all papers by the total number of publications in the database;
     compute the probability of each biomarker occurring with each outcome word by dividing the computed total number of times the outcome word appears after the biomarker word by the total number of publications in the database; and
     compute the association score for each biomarker and outcome word pair via normalized pointwise mutual information for each biomarker and outcome word pair using the probability of occurrence for each biomarker, the probability of occurrence for each outcome, and the probability each biomarker occurring with each outcome.

2. A method for calculating an association score between a biomarker and some outcome, comprising the steps of:
   receiving a clinical trial publication;
   scraping the clinical trial publications for biomarker and outcome word pairs;
   computing the total number of times the outcome word appears after the biomarker word in a window of words for all clinical trial publications;
   computing the probability of occurrence for each biomarker by dividing the computed total number of times each biomarker appears in all papers by the total number of publications in the database;
   computing the probability of occurrence for each outcome by dividing the computed total number of times each outcome appears in all papers by the total number of publications in the database;
   computing the probability of each biomarker occurring with each outcome word by dividing the computed total number of times the outcome word appears after the biomarker word by the total number of publications in the database; and computing the association score for each biomarker and outcome word pair via normalized pointwise mutual information for each biomarker and outcome word pair using the probability of occurrence for each biomarker, the probability of occurrence for each outcome, and the probability each biomarker occurring with each outcome.

* * * * *